US012622575B2

(12) United States Patent
Iwakawa

(10) Patent No.: US 12,622,575 B2
(45) Date of Patent: May 12, 2026

(54) BASE MEMBER WITH CURVATURE DETECTION FUNCTION, CURVATURE DETECTION SYSTEM, DEVICE COMPRISING BASE MEMBER WITH CURVATURE DETECTION FUNCTION, AND BALLOON CATHETER

(71) Applicant: Toray Industries, Inc., Tokyo-to (JP)

(72) Inventor: Kosei Iwakawa, Otsu (JP)

(73) Assignee: Toray Industries, Inc., Tokyo (JP)

( * ) Notice: Subject to any disclaimer, the term of this patent is extended or adjusted under 35 U.S.C. 154(b) by 928 days.

(21) Appl. No.: 17/794,647

(22) PCT Filed: Mar. 31, 2021

(86) PCT No.: PCT/JP2021/013783

§ 371 (c)(1), (2) Date: Jul. 22, 2022

(87) PCT Pub. No.: WO2021/201081

PCT Pub. Date: Oct. 7, 2021

(65) Prior Publication Data

US 2023/0076174 A1 Mar. 9, 2023

(30) Foreign Application Priority Data

Mar. 31, 2020 (JP) ................................ 2020-064484

(51) Int. Cl.
*A61B 1/005* (2006.01)
*A61B 18/04* (2006.01)
(Continued)

(52) U.S. Cl.
CPC .............. *A61B 1/009* (2022.02); *A61B 1/005* (2013.01); *A61B 1/0057* (2013.01); *A61B 18/04* (2013.01);
(Continued)

(58) Field of Classification Search
CPC .................. A61B 1/0057; A61B 1/009; A61B 2018/00577; A61B 18/1492;
(Continued)

(56) References Cited

U.S. PATENT DOCUMENTS 5,168,864 A * 12/1992 Shockey .............. A61B 1/0057 600/146
2013/0079614 A1* 3/2013 Harada .................. A61B 5/283 600/373
(Continued)

FOREIGN PATENT DOCUMENTS

JP H04-303411 A 10/1992
JP 06217929 A * 8/1994 ............... A61B 1/00
(Continued)

OTHER PUBLICATIONS

International Search Report dated Jun. 1, 2021 in counterpart International Application No. PCT/JP2021/013783.
(Continued)

*Primary Examiner* — Wesley G Harris
(74) *Attorney, Agent, or Firm* — DLA Piper LLP (US)

(57) ABSTRACT

A base member includes: a base member having a longitudinal direction; a first linear member extending in the longitudinal direction; and a second linear member extending in the longitudinal direction. The first linear member is fixed to the base member at a first position, and is movable with respect to the base member in the longitudinal direction, on one side of the first position in the longitudinal direction. The second linear member is fixed to the base member at a second position, and is movable with respect to the base member in the longitudinal direction, on the one side of the second position in the longitudinal direction. The base member is capable of detecting curvature of the base member between the first position and the second fixed
(Continued)

position based on change in a relative position between the first linear member and the second linear member.

9 Claims, 21 Drawing Sheets

(51) Int. Cl.

| | |
|---|---|
| ***A61B 18/14*** | (2006.01) |
| ***A61M 25/00*** | (2006.01) |
| *A61B 1/12* | (2006.01) |
| *A61B 18/00* | (2006.01) |
| *A61B 90/00* | (2016.01) |

(52) U.S. Cl.

CPC ......... *A61B 18/1492* (2013.01); *A61M 25/00* (2013.01); *A61B 1/128* (2013.01); *A61B 2018/0022* (2013.01); *A61B 2018/00821* (2013.01); *A61B 2018/046* (2013.01); *A61B 2090/0811* (2016.02)

(58) Field of Classification Search

CPC ........ A61B 2018/0022; A61B 1/00006; A61B 1/0016; A61B 18/04; A61B 1/0052; A61B 18/082; A61B 2090/067; A61B 2090/0811

See application file for complete search history.

(56) References Cited

U.S. PATENT DOCUMENTS

| | | | |
|---|---|---|---|
| 2017/0042412 | A1 | 2/2017 | Takemoto et al. |
| 2021/0093224 | A1 | 4/2021 | Morishima |

FOREIGN PATENT DOCUMENTS

| | | | | |
|---|---|---|---|---|
| JP | 2001-161636 | A | 6/2001 | |
| JP | 3917391 | B2 | 5/2007 | |
| JP | 4062935 | B2 | 3/2008 | |
| JP | 4222152 | B2 | 2/2009 | |
| JP | 4226040 | B2 | 2/2009 | |
| JP | 2013-085616 | A | 5/2013 | |
| JP | 2013-248119 | A | 12/2013 | |
| WO | WO-9410897 | A1 * | 5/1994 | ........... A61B 1/0052 |
| WO | WO-0113060 | A1 * | 2/2001 | ............. A61B 1/009 |
| WO | 2011/062079 | A1 | 5/2011 | |
| WO | 2012/132637 | A1 | 10/2012 | |
| WO | WO-2015194317 | A1 * | 12/2015 | ............. G02B 23/24 |
| WO | 2019/239545 | A1 | 12/2019 | |

OTHER PUBLICATIONS

Written Opinion dated Jun. 1, 2021 in counterpart International Application No. PCT/JP2021/013783.

Extended European Search Report dated Feb. 27, 2024, of counterpart European Patent Application No. 21778807.4.

* cited by examiner

BASE MEMBER WITH CURVATURE DETECTION FUNCTION, CURVATURE DETECTION SYSTEM, DEVICE COMPRISING BASE MEMBER WITH CURVATURE DETECTION FUNCTION, AND BALLOON CATHETER

TECHNICAL FIELD

This disclosure relates to a base member with a curvature detection function, a curvature detection system, a device comprising the base member with the curvature detection function, and a balloon catheter.

BACKGROUND

Catheter ablation therapy is a treatment method that uses a catheter inserted into a body to ablate a target site in the human body. As an example, a target site is destroyed by ablation to treat diseases such as arrhythmia due to atrial fibrillation, endometriosis, cancer and the like. As disclosed in JP 4062935 B2, JP 4226040 B2 and JP 4222152 B2, a balloon catheter having a distal end to which a balloon is attached is known as a catheter used for catheter ablation therapy.

A balloon catheter has a catheter shaft inserted into a human body, and a balloon provided at a distant end of the catheter shaft. The catheter shaft is formed of a long flexible base member. The catheter shaft is inserted into a human body and is guided to a vicinity of a target site, and then a liquid is supplied into the balloon through an inside space of the catheter shaft so that the balloon is inflated. Since a temperature of the liquid in the balloon has been controlled, a surface temperature of the balloon can be controlled. By bringing the balloon whose surface temperature has been adjusted to a predetermined one into contact with a circumferential target site, e.g., a connection of a vein to an atrium, the circumferential target site can be ablated at once.

When a distant end portion of the balloon catheter is curved, it may cause inconveniences such as loss of control of the balloon surface temperature. Thus, to be able to detect the curvature of a distant end portion of a balloon catheter is one of the needs for balloon catheters. Other devices including a long flexible base member (for example, catheter of another type, medical endoscope, industrial endoscope and the like) have a similar need. Although a distant end portion of a balloon catheter can be seen through a radioscopic image, the radioscopic image provides only two-dimensional information. Thus, it is often difficult to find out, from a radioscopic image, whether the distant end portion is curved, and/or in which direction the distant end portion is curved. JP 3917391 B2 discloses a medical endoscope that detects curvature of a long base member by using an optical fiber disposed in the base member. However, the base member is required to have a certain degree of thickness (external dimensions) to detect curvature by means an optical fiber disposed in the base member. Thus, it is difficult to apply the aforementioned curvature detection method to a device such as a balloon catheter on which severe restrictions on external dimensions of a base member (catheter shaft) are imposed.

It could therefore be helpful to detect the curvature of a base member with increase in external dimensions of the base member minimized.

SUMMARY

I thus provide:

A base member with a curvature detection function comprises: a base member having a longitudinal direction; a first linear member extending in the longitudinal direction; and a second linear member extending in the longitudinal direction. The first linear member is fixed to the base member at a first fixed position, and is relatively movable with respect to the base member in the longitudinal direction, on one side of the first fixed position in the longitudinal direction. The second linear member is fixed to the base member at a second fixed position different from the first fixed position, and is relatively movable with respect to the base member in the longitudinal direction, on the one side of the second fixed position in the longitudinal direction. The base member with the curvature detection function is capable of detecting curvature of the base member between the first fixed position and the second fixed position based on change in a relative position between the first linear member and the second linear member.

In the base member with the curvature detection function, the first linear member and the second linear member may be disposed in one or more lumens provided in the base member.

The first linear member and the second linear member may be disposed in separate lumens.

The base member may be a cylindrical member having a wall delimiting a hollow.

The first linear member and the second linear member may be disposed in one or more lumens provided in the base member, and the one or more lumens may be formed in the wall.

Markers indicating a relative position between the first linear member and the second linear member may be provided on the first linear member and the second linear member.

The base member with the curvature detection function may comprise a third linear member and a fourth linear member, the third and fourth linear members extending along the longitudinal direction at a position/positions different from a position/positions of the first linear member and the second linear member in a circumferential direction of the wall, wherein: the third linear member is fixed to the base member at the first fixed position, and is relatively movable with respect to the base member in the longitudinal direction, on the one side of the first fixed position in the longitudinal direction; the fourth linear member is fixed to the base member at the second fixed position, and is relatively movable with respect to the base member in the longitudinal direction, on the one side of the second fixed position in the longitudinal direction; and the base member with the curvature detection function is capable of detecting curvature of the base member between the first fixed position and the second fixed position based on change in a relative position between (ends on the above one side of) the third linear member and the fourth linear member.

The third linear member and the fourth linear member may be disposed in other one or more lumens provided at a position/positions different from a position/positions of the one or more lumens for the first linear member and the second linear member in the circumferential direction of the wall.

In addition, markers indicating a relative position between the third linear member and the fourth linear member may be provided on the third linear member and the fourth linear member.

Alternatively, a curvature detection system comprises: the aforementioned base member with the curvature detection function; and a sensor configured to detect change in a relative position between the first linear member and the second linear member.

A device comprises the aforementioned base member with the curvature detection function.

A balloon catheter comprises:

a balloon;

a catheter shaft having an outer cylinder shaft connected to a proximal end of the balloon, and an inner cylinder shaft extending into the balloon to be connected to a distal end of the balloon, wherein the inner cylinder shaft extends inside the outer cylinder shaft, and a gap between the inner cylinder shaft and the outer cylinder shaft serves as a liquid delivery path in communication with an inside space of the balloon; and a heating member for heating a liquid in the balloon, the heating member being disposed on an outer circumferential surface of the inner cylinder shaft in the balloon. The inner cylinder shaft is the aforementioned base member with the curvature detection function.

I thus make it possible to detect the curvature of the base member with increase in external dimensions of the base member minimized.

Figure 1:
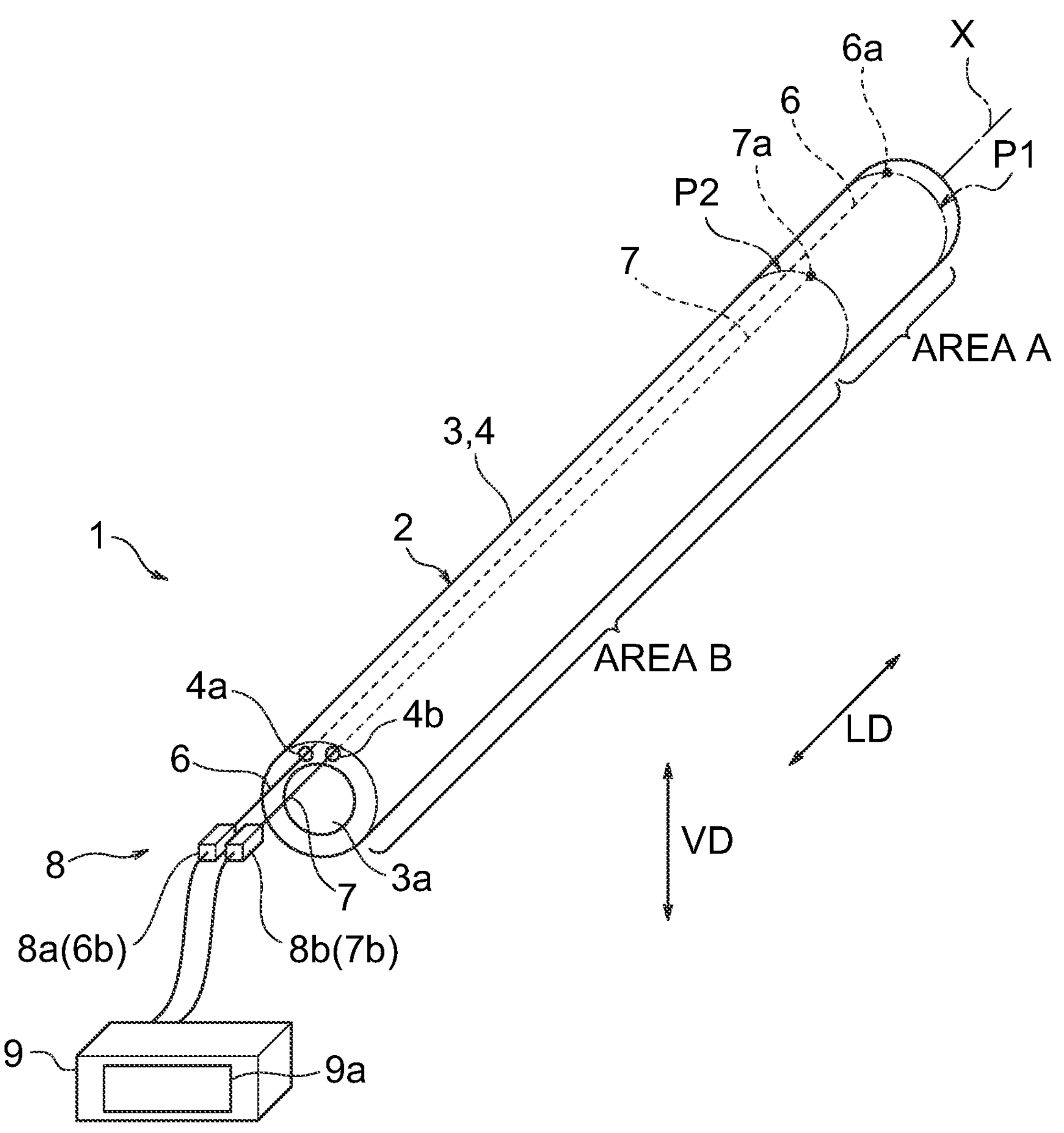
FIG. 1 is view for describing a first example, and is a perspective view showing a base member with a curvature detection function and a curvature detection system.

1, 11, 101 Curvature detection system
2, 12, 102 Base member with curvature detection function
3 Base member
3*a* Hollow
4 Wall
4*a*, 4*b*, 4*c*, 4*d*, 4*e* Lumen
6 First linear member
7 Second linear member
16 Third linear member
17 Fourth linear member
108 Fifth linear member
20 Balloon catheter system
21 Balloon catheter
25 Balloon
30 Outer cylinder shaft
35 Inner cylinder shaft
40 Heating member
41 Coil electrode
45 Temperature sensor
70 Heating device
75 Agitation device
LD Longitudinal direction
LP Liquid delivery path

DETAILED DESCRIPTION

First Example

A first example will be described hereunder with reference to specific configurations shown in the drawings. In the drawings attached to the specification, a scale dimension, an aspect ratio and so on are changed and exaggerated from the actual ones, for the convenience of easiness in illustration and understanding. In addition, terms used herein to specify shapes, geometric conditions and their degrees, e.g., “parallel,” “orthogonal,” “same” or the like, and values of a length and an angle are not limited to their strict definitions, but construed to include a range capable of exerting a similar function.

A curvature detection system 1 shown in FIG. 1 has a base member with a curvature detection function 2, a distance displacement sensor 8, and a display device 9. In addition, the base member with the curvature detection function 2 has a base member 3 having a longitudinal direction LD, a first linear member 6 extending along the longitudinal direction LD, and a second linear member 7 extending in the longitudinal direction LD.

The base member 3 can be curved. The base member 3 can be made of various materials such as metal, ceramic, resin and the like, depending on an application of the base member with the curvature detection function 2.

In the illustrated example, the base member 3 is a cylindrical member having a wall 4 delimiting a hollow 3*a*. It goes without saying that, not limited to the cylindrical shape, the base member 3 can have another shape such as a plate-like shape, a pillar shape or the like.

The base member 3 is provided with a first lumen 4*a* and a second lumen 4*b* which extend adjacently to each other in the longitudinal direction LD. The first lumen 4*a* and the second lumen 4*b* are formed in the wall 4 of the base member 3.

The first linear member 6 is disposed in the first lumen 4*a*, and the second linear member 7 is disposed in the second lumen 4*b*. Since the linear member 6, 7 are disposed in the lumens 4*a*, 4*b*, the risk of damaging the linear members 6, 7 is reduced. In addition, since the linear members 6, 7 are disposed in the lumens 4*a*, 4*b* separated from one another, the risk of causing the linear members 6, 7 to be entangled is reduced.

The first linear member 6 has a first end 6*a* and a second end 6*b* positioned on one side of the first end 6*a* in the longitudinal direction. The first end 6*a* of the first linear member 6 is fixed to a first fixed position P1 of the base member 3 in the first lumen 4*a*. The rest part of the first linear member 6, which includes the second end 6*b*, is disposed in the first lumen 4*a* so that the rest part is relatively movable with respect to the base member 3 in the longitudinal direction LD.

The second linear member 7 also has a first end 7*a* and a second end 7*b* positioned on the one side of the first end 7*a* in the longitudinal direction LD. The first end 7*a* of the second linear member 7 is fixed to a second fixed position P2 of the base member 3 in the second lumen 4*b*. The rest part of the second linear member 7, which includes the second end 7*b*, is disposed in the second lumen 4*b* so that the rest part is relatively movable with respect to the base member 3 and the first linear member 6 in the longitudinal direction LD. The second fixed position P2 is located at a position apart from the first fixed position P1 in the longitudinal direction Ld. In the illustrated example, the second fixed poison P2 is positioned on the one side of the first fixed position P1 along the longitudinal direction LD.

The first linear member 6 and the second linear member 7 are made of a low-stretch material compared to the base member 3 and can be curved along the base member 3 when it is curved. The first linear member 6 and the second linear member 7 can be made of various materials such as metal, resin or the like, depending on an application of the base member with the curvature detection function 2. The first linear member 6 and the second linear member 7 are preferably made of the same material.

Figure 2:
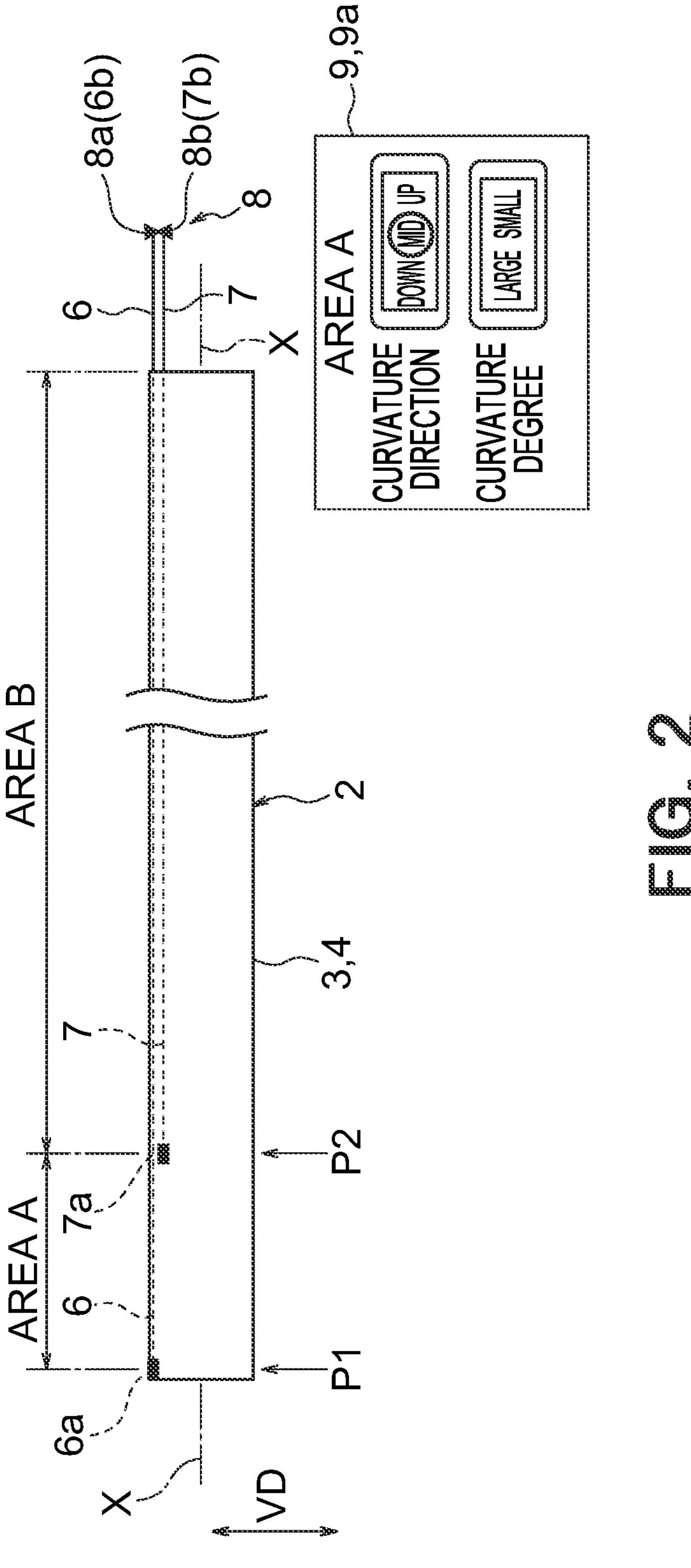
FIG. 2 is a side view of the base member with the curvature detection function of FIG. 1.

In the illustrated example, lengths of the first linear member 6 and the second linear member 7 are determined such that, as shown in FIGS. 1 and 2, the second end 6*b* of the first linear member 6 and the second end 7*b* of the second linear member 7 are located at the same position in the longitudinal direction LD, with the base member 3 not curved at any position in the longitudinal direction LD. However, as described later, this disclosure is not limited to this example, as long as it is possible to detect change in a relative position between the second end 6*b* of the first linear member 6 and the second end 7*b* of the second linear member 7.

The base member with the curvature detection function 2 as structured above can detect curvature of the base member 3 between the first fixed position P1 and the second fixed position P2, based on change in a relative position between the second ends 6*b*, 7*b* of the first linear member 6 and the second linear member 7. In particular, curvature of the base member 3 in a vertical direction VD can be detected.

In the below description, a side of the base member 3, on which the first linear member 6 and the second linear member 7 are provided, is referred to as "upper side," and a side opposed to the upper side is referred to as "lower side." In addition, a direction directed from the lower side toward the upper side is referred to as "upward," and a direction directed from the upper side toward the lower side is referred to as "downward." In FIGS. 2 to 6, although the first linear member 6 and the second linear member 7 are shown at different positions in the vertical direction for the sake of facilitating understanding, note that the first linear member 6 and the second linear member 7 are located at positions that are overlapped with each other in a side view of the base member with the curvature detection function 2.

With reference to FIGS. 2 to 6, relative movement between the second ends 6*b*, 7*b* of the first linear member 6 and the second linear member 7 due to curvature of the base member 3 is described.

As shown in FIG. 2, when the base member 3 is not curved at any position in the longitudinal direction LD, the second end 6*b* of the first linear member 6 and the second end 7*b* of the second linear member 7 are located at the same position in the longitudinal direction LD, as described above.

Figure 3:
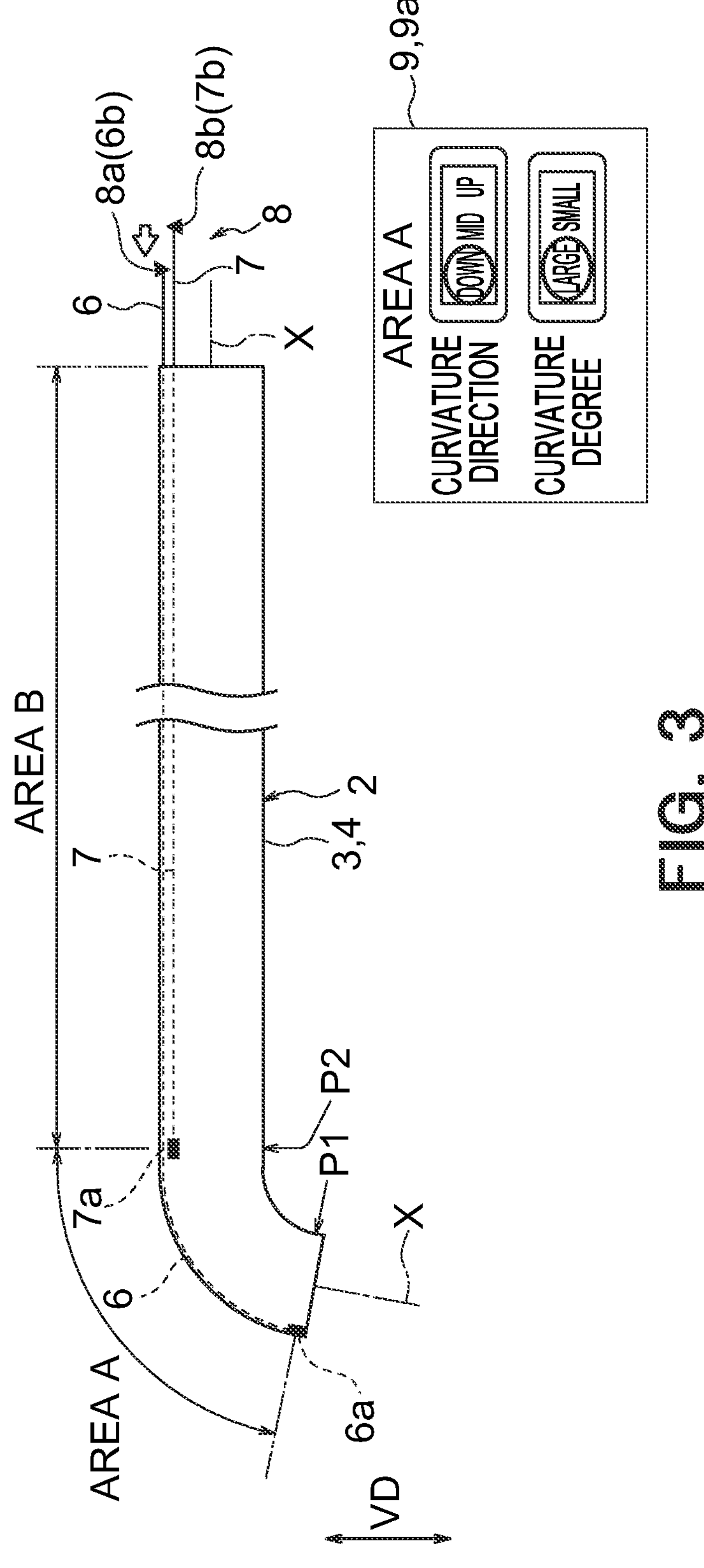
FIG. 3 is a view corresponding to FIG. 2, showing the base member with the curvature detection function which is curved downward in an area A.

As shown in FIG. 3, when the base member 3 is curved downward in an area A between the first fixed position P1 and the second fixed position P2, the upper side region of the area A (the region where the first linear member 6 is disposed) is stretched due to the curvature. Thus, the second end 6*b* of the first linear member 6, which extends in the area A, moves with respect to the base member 3 to the other side (left side in FIG. 3) in the longitudinal direction LD. On the other hand, the second end 7*b* of the second linear member 7, which does not extend in the area A, does not move with respect to the base member 3. As a result, the second end 6*b* of the first linear member 6 moves relatively with respect to the second end 7*b* of the second linear member 7 to the other side (left side in FIG. 3) in the longitudinal direction LD and the relative position between the second end 6*b* of the first linear member 6 and the second end 7*b* of the second linear member 7 changes.

Figure 4:
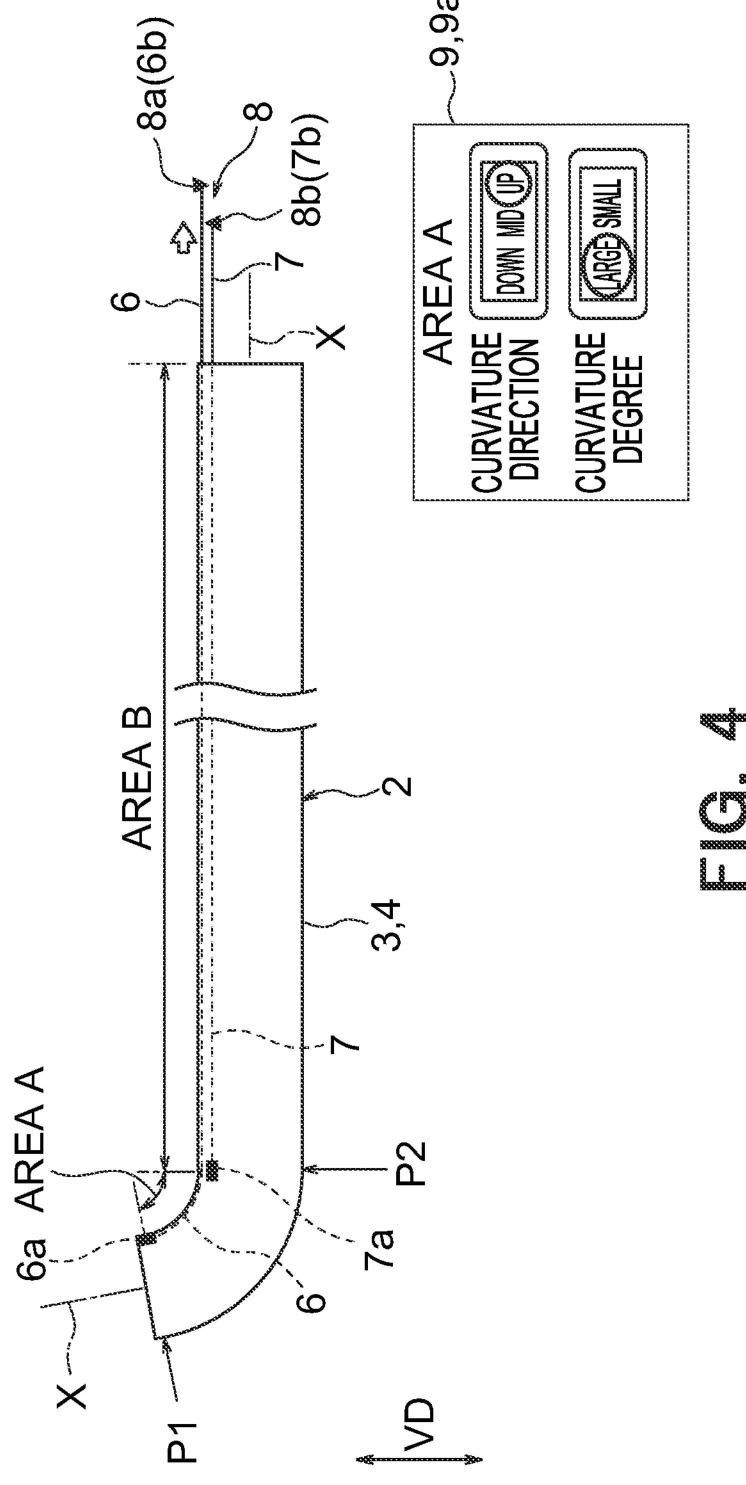
FIG. 4 is a view corresponding to FIG. 2, showing the base member with the curvature detection function which is curved upward in the area A.

In addition, as shown in FIG. 4, when the base member 3 is curved upward in the area A, the upper side region of the area A (the region where the first linear member 6 is disposed) is contracted due to the curvature. Thus, the second end 6*b* of the first linear member 6, which extends in the area A, moves with respect to the base member 3 to the one side (right side in FIG. 4) in the longitudinal direction LD. On the other hand, the second end 7*b* of the second linear member 7, which does not extend in the area A, does not move with respect to the base member 3. As a result, the second end 6*b* of the first linear member 6 moves relatively with respect to the second end 7*b* of the second linear member 7 to the one side (right side in FIG. 4) in the longitudinal direction LD and the relative position between the second end 6*b* of the first linear member 6 and the second end 7*b* of the second linear member 7 changes.

Figure 5:
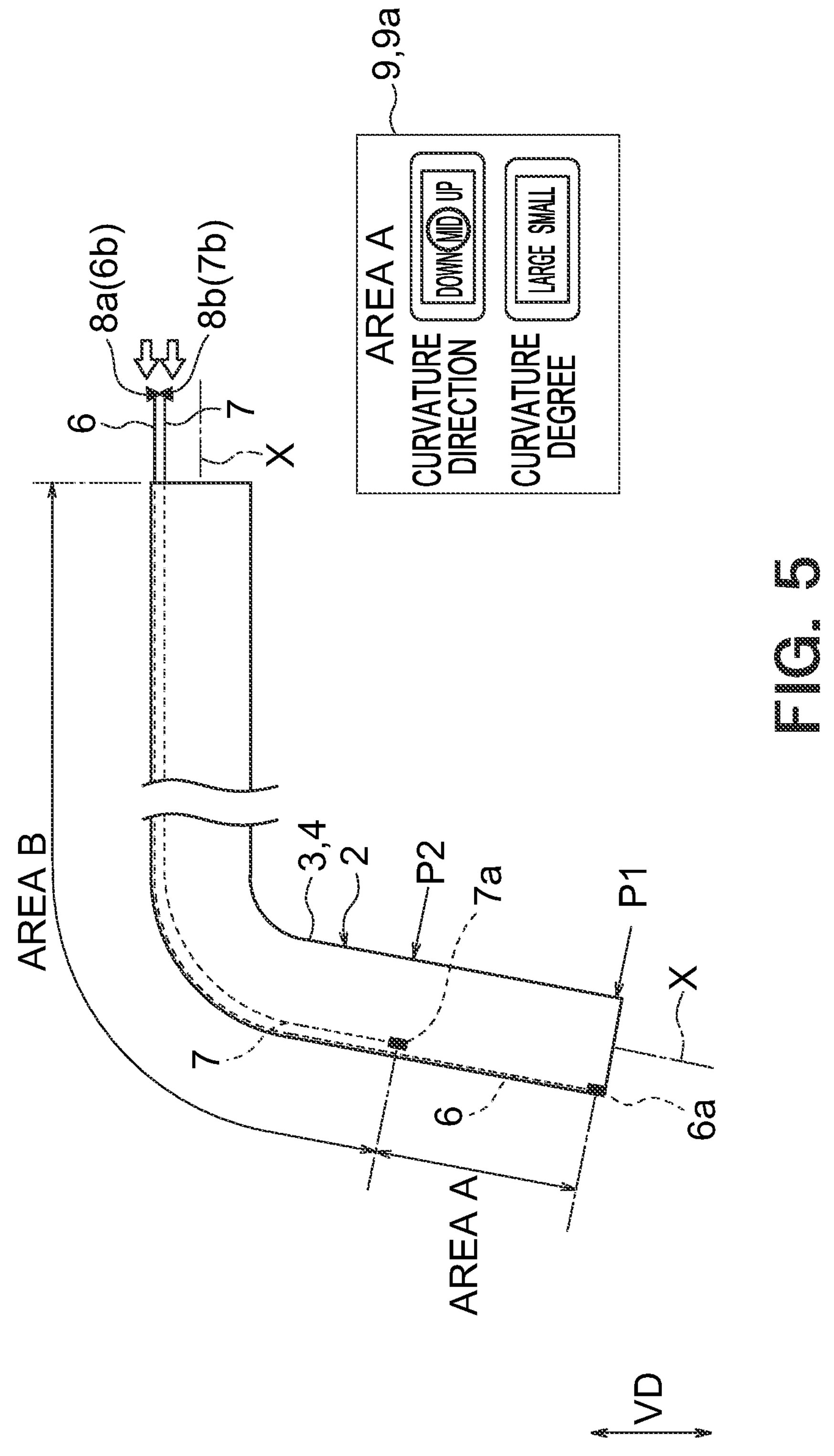
FIG. 5 is a view corresponding to FIG. 2, showing the base member with the curvature detection function which is curved downward in an area B.

In addition, as shown in FIG. 5, when the base member 3 is curved downward in an area B which is positioned on the one side (right side in FIG. 5) of the second fixed position P2 in the longitudinal direction LD, the upper side region of the area B (the region where the first linear member 6 and the second linear member 7 are disposed) is stretched due to the curvature. Thus, the second end 6*b* of the first linear member 6, which extends in the area B, moves with respect to the base member 3 to the other side (left side in FIG. 5) in the longitudinal direction LD. Similarly, the second end 7*b* of the second linear member 7, which extends in the area B, moves with respect to the base member 3 to the other side (left side in FIG. 5) in the longitudinal direction LD. A distance moved by the second end 7*b* of the second linear member 7 with respect to the base member 3 is the same as a distance moved by the second end 6*b* of the first linear member 6 with respect to the base member 3. As a result, the relative position between the second end 6*b* of the first linear member 6 and the second end 7*b* of the second linear member 7 does not change.

Figure 6:
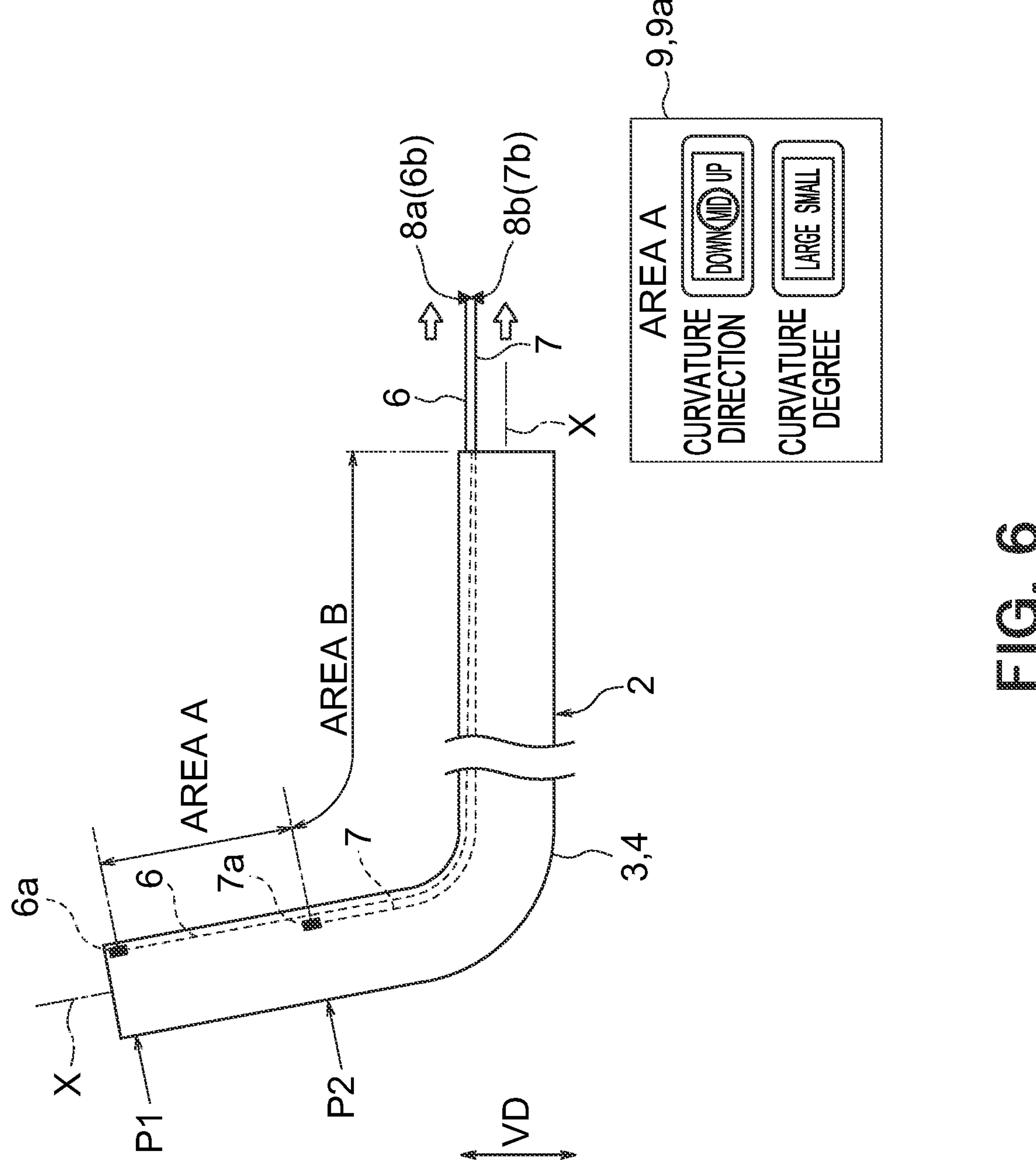
FIG. 6 is a view corresponding to FIG. 2, showing the base member with the curvature detection function which is curved upward in the area B.

In addition, as shown in FIG. 6, when the base member 3 is curved upward in the area B, the upper side region of the area B (the region where the first linear member 6 and the second linear member 7 are disposed) is contracted due to the curvature. Thus, the second end 6*b* of the first linear member 6, which extends in the area B, moves with respect to the base member 3 to the one side (right side in FIG. 6) in the longitudinal direction LD. Similarly, the second end 7*b* of the second linear member 7, which extends in the area B, moves with respect to the base member 3 to the one side (right side in FIG. 6) in the longitudinal direction LD. A distance moved by the second end 7*b* of the second linear member 7 with respect to the base member 3 is the same as a distance moved by the second end 6*b* of the first linear member 6 with respect to the base member 3. As a result, the relative position between the second end 6*b* of the first linear member 6 and the second end 7*b* of the second linear member 7 does not change.

Therefore, it is possible to detect whether the base member 3 is curved in the area A by detecting change in a relative position between the second end 6*b* of the first linear member 6 and the second end 7*b* of the second linear member 7. In addition, it is possible to detect a direction of curvature (upward or downward) of the base member in the area A by detecting a direction of displacement of the second end 6*b* of the first linear member 6 with respect to the second end 7*b* of the second linear member 7.

Further, when the base member 3 is curved in the area A, the amount of displacement of the second end 6*b* of the first linear member 6 with respect to the second end 7*b* of the second linear member 7 depends on a degree of the curvature of the area A (in other words, an angle of a direction in which a center axis X of the base member 3 at the fixed position P2 extends, with respect to a direction in which the center axis X of the base member 3 at the fixed position P1 extends). Thus, the degree of curvature of the base member 3 in the area A can be detected by detecting the amount of the displacement of the second end 6*b* with respect to the second end 7*b*.

Next, the distance displacement sensor 8 is described. The distance displacement sensor 8 detects change in a relative position between the second ends 6*b*, 7*b* of the first linear member 6 and the second linear member 7. The distance displacement sensor 8 includes a first sensor 8*a* and a second sensor 8*b*, and is capable of detecting change in a relative position between the first sensor 8*a* and the second sensor 8*b*. The first sensor 8*a* is fixed to the second end 6*b* of the first linear member 6, and the second sensor 8*b* is fixed to the second end 7*b* of the second linear member 7. The distance displacement sensor 8 is electrically connected to the display device 9. When a relative position of the first sensor 8*a* with respect to the second senor 8*b* changes, the distance displacement sensor 8 inputs, to the display device 9, a signal corresponding to a direction and the amount of displacement of the first sensor 8*a* with respect to the second sensor 8*b*.

The display device 9 determines the direction and the degree of curvature of the base member 3 in the area A based on the signal inputted by the distance displacement sensor 8, and displays them on a display 9*a*.

In the illustrated example, the display device 9 displays the curvature direction detected by the distance displacement sensor 8 as "UP," "MID" or "DOWN." Specifically, when the base member 3 is not curved in the area A as shown in FIGS. 2, 5 and 6, the display device 9 indicates the curvature direction as "MID." When the base member 3 is curved downward in the area A as shown in FIG. 3, the display device 9 indicates the curvature direction as "DOWN." When the base member 3 is curved upward in the area A as shown in FIG. 4, the display device 9 indicates the curvature direction as "UP."

In addition, in the illustrated example, the display device 9 displays the curvature degree detected by the distance displacement sensor 8 as "LARGE" or "SMALL." Specifically, when the amount of displacement of the first sensor 8*a* with respect to the second sensor 8*b* (thus the amount of displacement of the second end 6*b* of the first linear member 6 with respect to the second end 7*b* of the second linear member 7) is zero (this is the examples of FIGS. 2, 5 and 6), the display device 9 does not display the curvature degree. When the amount of displacement of the first sensor 8*a* with respect to the second sensor 8*b* is greater than 0 and less than a predetermined value, the display device 9 indicates the curvature degree as "SMALL." When the amount of displacement of the first sensor 8*a* with respect to the second sensor 8*b* is equal to or greater than the predetermined value, the display device 9 indicates the curvature degree as "LARGE."

Second Example

Next, a curvature detection system 11 according to a second example is described with reference to FIGS. 7 to 12.

An example shown in FIGS. 7 to 12 differs from the curvature detection system 1 shown in FIGS. 1 to 6 in that a base member with a curvature detection function 12 further has a third linear member 16 extending in a longitudinal direction LD, a fourth linear member 17 extending in the longitudinal direction LD, and a second distance displacement sensor 18. Other configurations are substantially the same as those of the curvature detection system 1 shown in FIGS. 1 to 6. In the example shown in FIGS. 7 to 12, the same numerals are given to the same parts as those of the first example shown in FIGS. 1 to 6, and detailed description thereof is omitted.

In the example shown in FIGS. 7 to 12, a base member 3 further has a third lumen 4*c* and a fourth lumen 4*d* which extend adjacently to each other in the longitudinal direction LD. The third lumen 4*c* and the fourth lumen 4*d* are formed in a wall 4 of the base member 3.

Figure 7:
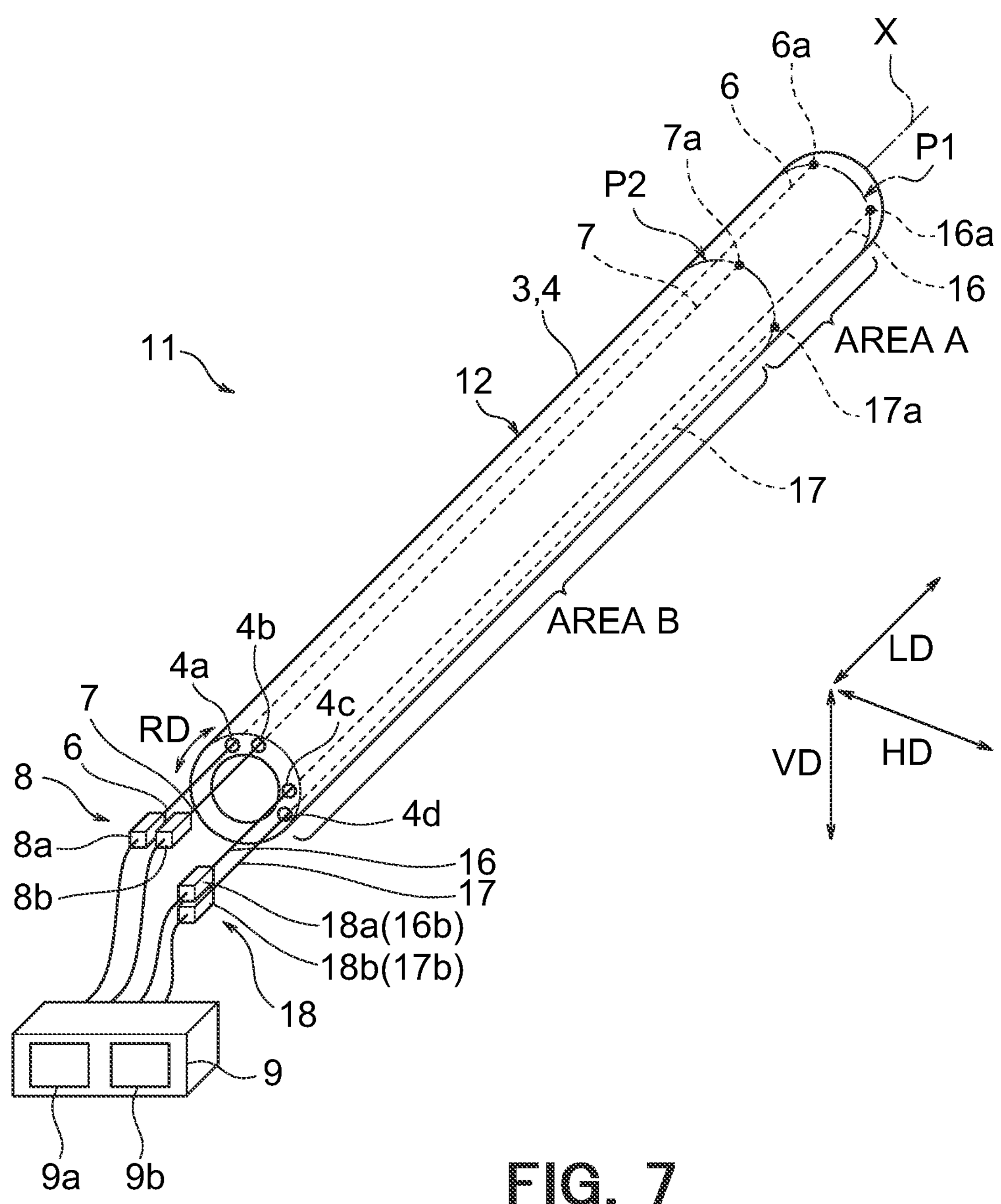
FIG. 7 is a view for describing a second example, and is a perspective view showing a base member with a curvature detection function and a curvature detection system.

As shown in FIG. 7, the third lumen 4*c* and the fourth lumen 4*d* are located at positions different from the positions of the first lumen 4*a* and the second lumen 4*b* in a circumferential direction RD of the cylindrical part 4 of the base member 3. The third lumen 4*c* and the fourth lumen 4*d* are apart from the first lumen 4*a* and the second lumen 4*b* by 90 degrees clockwise around the center axis X of the base member 2, when the base member 3 is observed from one end (an end on the area B side) in the longitudinal direction LD.

The third linear member 16 is disposed in the third lumen 4*c*, and the fourth linear member 17 is disposed in the fourth lumen 4*d*. Since the linear member 16, 17 are disposed in the lumens 4*c*, 4*d*, the risk of damaging the linear members 16, 17 is reduced. In addition, since the linear members 16, 17 are disposed in the lumens 4*c*, 4*d* separated from one another, the risk of causing the linear members 16, 17 to be entangled is reduced.

The third linear member 16 has a first end 16*a* and a second end 16*b* positioned on one side of the first end 16*a* in the longitudinal direction LD. The first end 16*a* of the third linear member 16 is fixed to the first fixed position P1 of the base member 3 in the third lumen 4*c*. The rest part of the third linear member 16, which includes the second end 16*b*, is disposed in the third lumen 4*c* so that the rest part is relatively movable with respect to the base member 3 in the longitudinal direction LD.

The fourth linear member 17 also has a first end 17*a* and a second end 17*b* positioned on the one side of the first end 17*b* in the longitudinal direction LD. The first end 17*a* of the fourth linear member 17 is fixed to the second fixed position P2 of the base member 3 in the fourth lumen 4*d*. The rest part of the fourth linear member 17, which includes the second end 17*b*, is disposed in the fourth lumen 4*d* so that the rest part is relatively movable with respect to the base member 3 and the third linear member 16 in the longitudinal direction LD.

The third linear member 16 and the fourth linear member 17 are made of a low-stretch material compared to the base member 3 and can be curved along the base member 3 when it is curved. Similarly to the first linear member 6 and the second linear member 7, the third linear member 16 and the fourth linear member 17 can be made of various materials such as metal, resin or the like, depending on an application of the base member with the curvature detection function 12. The third linear member 16 and the fourth linear member 17 are preferably made of the same material.

Figure 8:
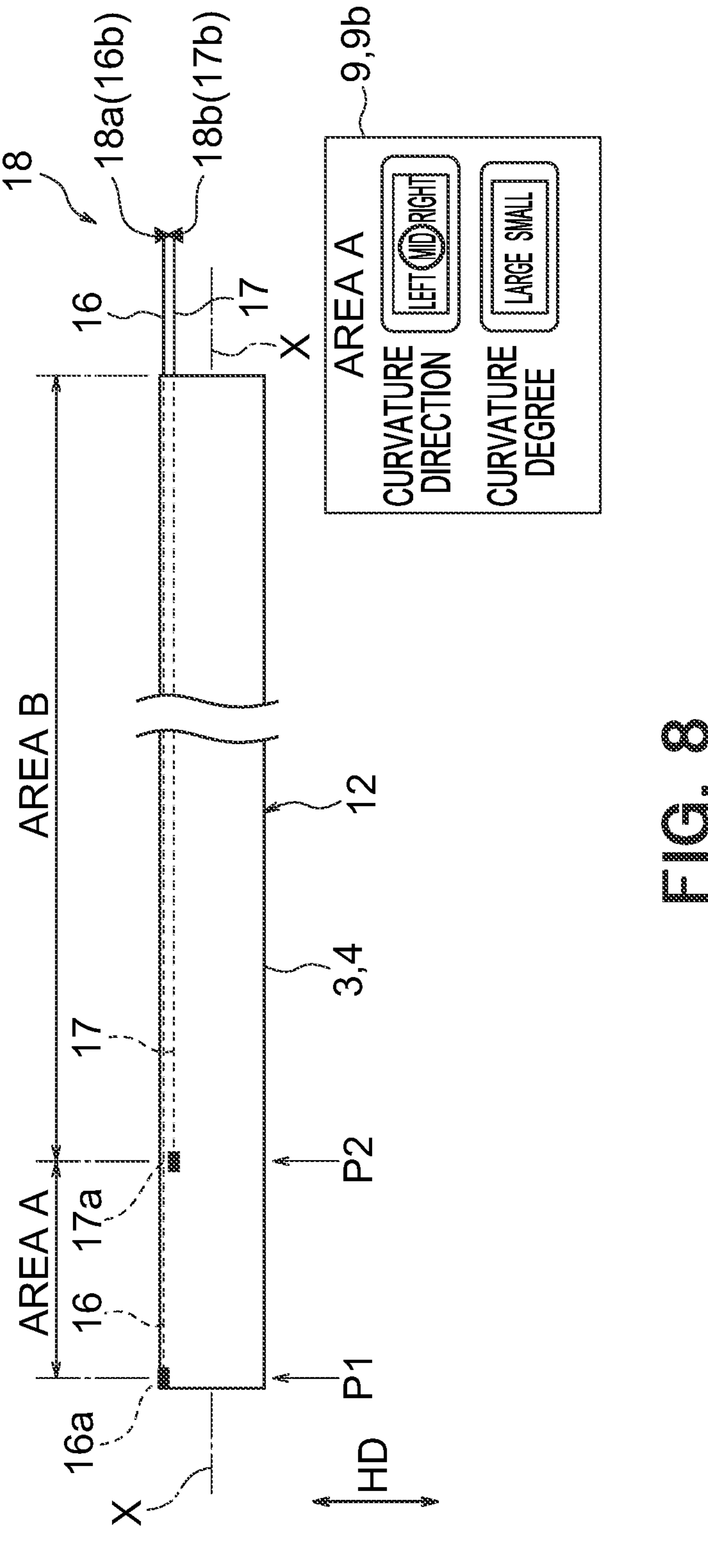
FIG. 8 is a top view of the base member with the curvature detection function of FIG. 7.

In the illustrated example, lengths of the third linear member 16 and the fourth linear member 17 are determined such that, as shown in FIGS. 7 and 8, the second end 16*b* of the third linear member 16 and the second end 17*b* of the fourth linear member 17 are located at the same position in the longitudinal direction LD, with the base member 3 not curved at any position in the longitudinal direction LD. However, as described later, this disclosure is not limited to this example, as long as it is possible to detect change in a relative position between the second end 16*b* of the third linear member 16 and the second end 17*b* of the fourth linear member 17.

The base member with the curvature detection function 12 as structured above can detect curvature of the base member 3 between the first fixed position P1 and the second fixed position P2, based on change in a relative position between the second ends 16*b*, 17*b* of the third linear member 16 and the fourth linear member 17. In particular, curvature of the base member 3 in a horizontal direction HD can be detected.

In the below description, a side of the base member 3, on which the third linear member 16 and the fourth linear member 17 are provided, is referred to as "right side," and a side opposed to the right side is referred to as "left side." In addition, a direction directed from the left side toward the right side is referred to as "rightward," and a direction directed from the right side toward the left side is referred to as "leftward." In FIGS. 8 to 12, although the third linear member 16 and the fourth linear member 17 are shown at different positions in the horizontal direction for the sake of facilitating understanding, note that the third linear member 16 and the fourth linear member 17 are located at positions that are overlapped with each other in a top view of the base member with the curvature detection function 12.

With reference to FIGS. 8 to 12, relative movement between the third linear member 16 and the fourth linear member 17 due to curvature of the base member 3 is described.

As shown in FIG. 8, when the base member 3 is not curved at any position in the longitudinal direction LD, the second end 16*b* of the third linear member 16 and the second end 17*b* of the fourth linear member 17 are located at the same position in the longitudinal direction LD, as described above.

Figure 9:
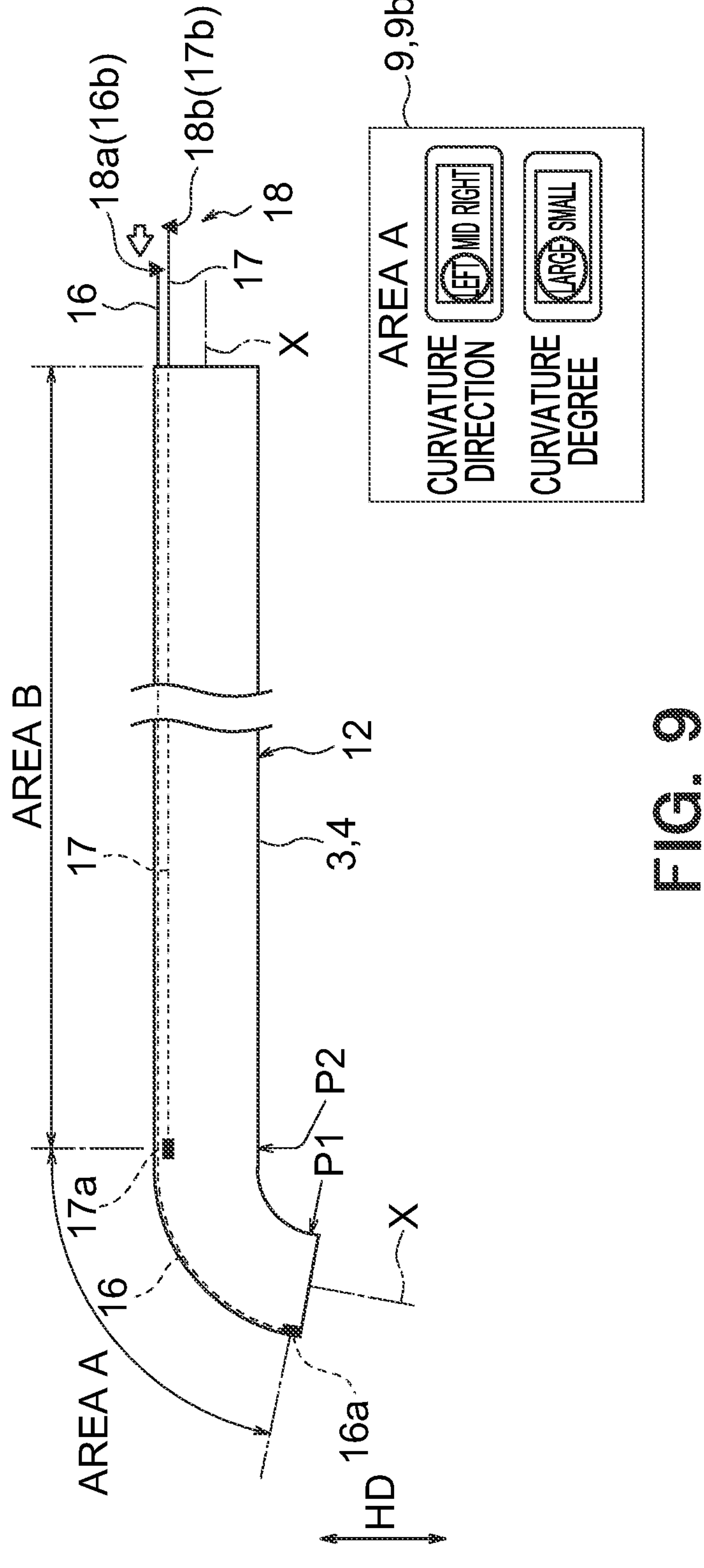
FIG. 9 is a view corresponding to FIG. 8, showing the base member with the curvature detection function which is curved leftward in an area A.

As shown in FIG. 9, when the base member 3 is curved leftward in the area A, the right side region of the area A (the region where the third linear member 16 is disposed) is stretched due to the curvature. Thus, the second end 16*b* of the third linear member 16, which extends in the area A, moves with respect to the base member 3 to the other side (left side in FIG. 9) in the longitudinal direction LD. On the other hand, the second end 17*b* of the fourth linear member 17, which does not extend in the area A, does not move with respect to the base member 3. As a result, the second end 16*b* of the third linear member 16 moves relatively with respect to the second end 17*b* of the fourth linear member 17 to the other side (left side in FIG. 9) in the longitudinal direction LD and the relative position between the second end 16*b* of the third linear member 16 and the second end 17*b* of the fourth linear member 17 changes.

Figure 10:
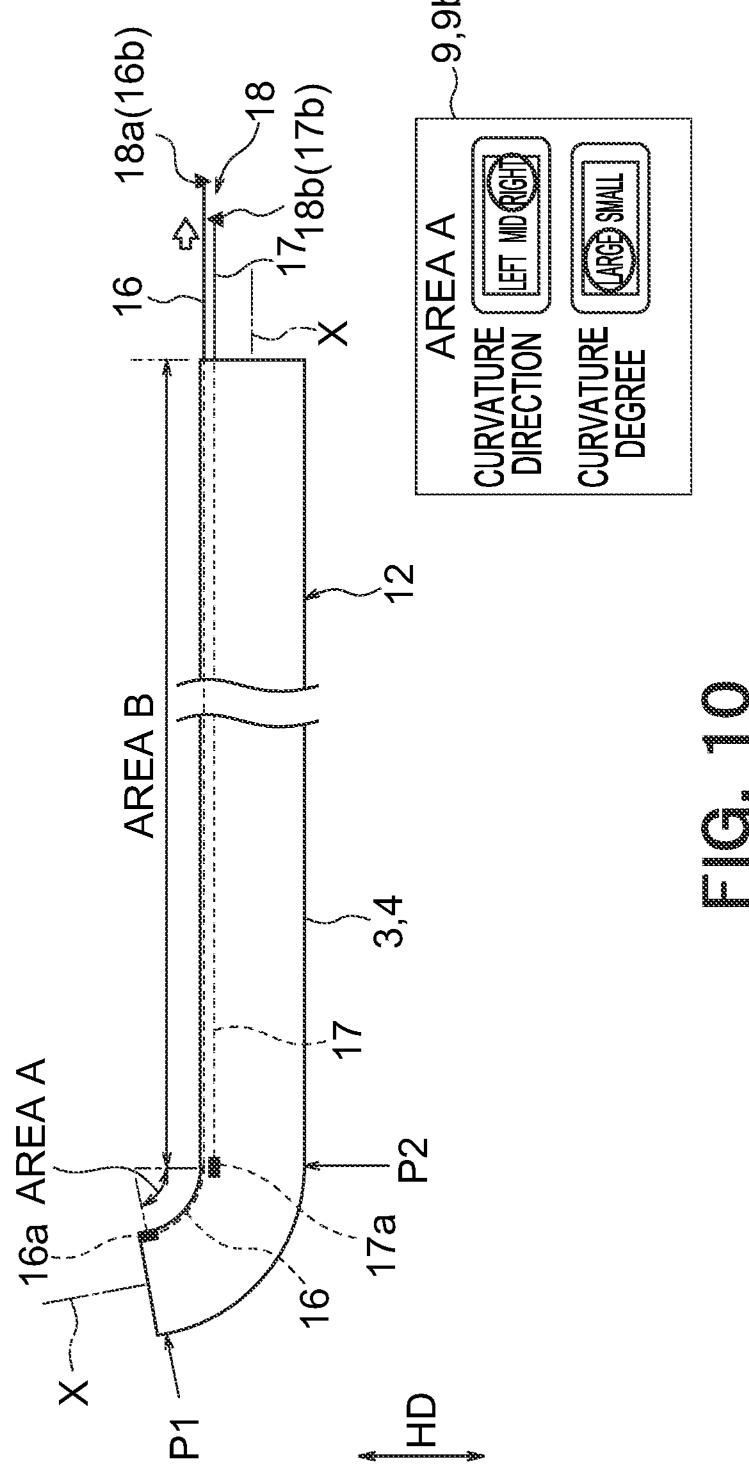
FIG. 10 is a view corresponding to FIG. 8, showing the base member with the curvature detection function which is curved rightward in the area A.

In addition, as shown in FIG. 10, when the base member 3 is curved rightward in the area A, the right side region of the area A (the region where the third linear member 16 is disposed) is contracted due to the curvature. Thus, the second end 16*b* of the third linear member 16, which extends in the area A, moves with respect to the base member 3 to the one side (right side in FIG. 10) in the longitudinal direction LD. On the other hand, the second end 17*b* of the fourth linear member 17, which does not extend in the area A, does not move with respect to the base member 3. As a result, the second end 16*b* of the third linear member 16 moves relatively with respect to the second end 17*b* of the fourth linear member 17 to the one side (right side in FIG. 10) in the longitudinal direction LD and the relative position between the second end 16*b* of the third linear member 16 and the second end 17*b* of the fourth linear member 17 changes.

Figure 11:
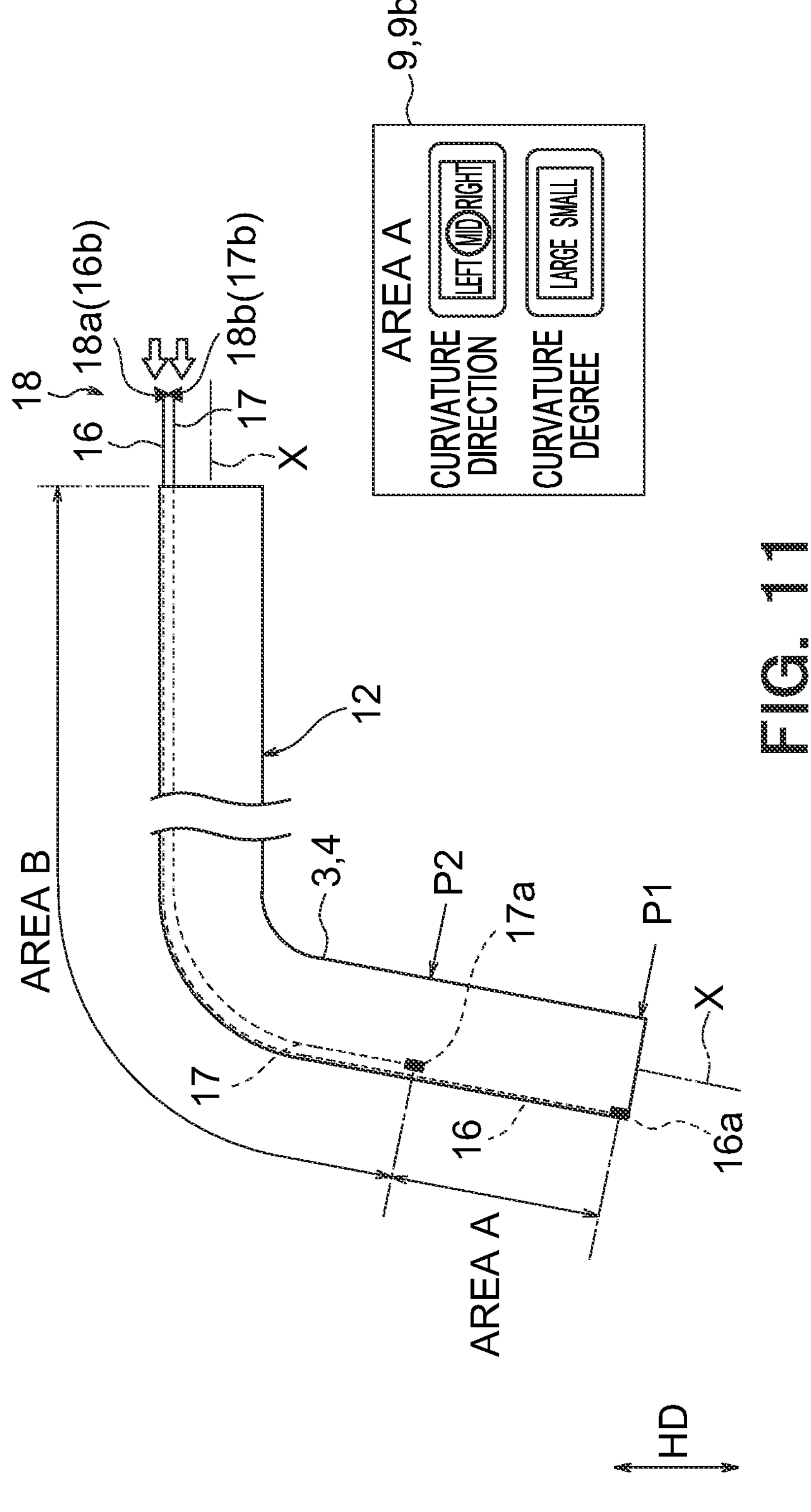
FIG. 11 is a view corresponding to FIG. 8, showing the base member with the curvature detection function which is curved leftward in an area B.

In addition, as shown in FIG. 11, when the base member 3 is curved leftward in the area B, the right side region of the area B (the region where the third linear member 16 and the fourth linear member 17 are disposed) is stretched due to the curvature. Thus, the second end 16*b* of the third linear member 16, which extends in the area B, moves with respect to the base member 3 to the other side (left side in FIG. 11) in the longitudinal direction LD. Similarly, the second end 17*b* of the fourth linear member 17, which extends in the area B, moves with respect to the base member 3 to the other side (left side in FIG. 11) in the longitudinal direction LD. A distance moved by the second end 17*b* of the fourth linear member 17 with respect to the base member 3 is the same as a distance moved by the second end 16*b* of the third linear member 16 with respect to the base member 3. As a result, the relative position between the second end 16*b* of the third linear member 16 and the second end 17*b* of the fourth linear member 17 does not change.

Figure 12:
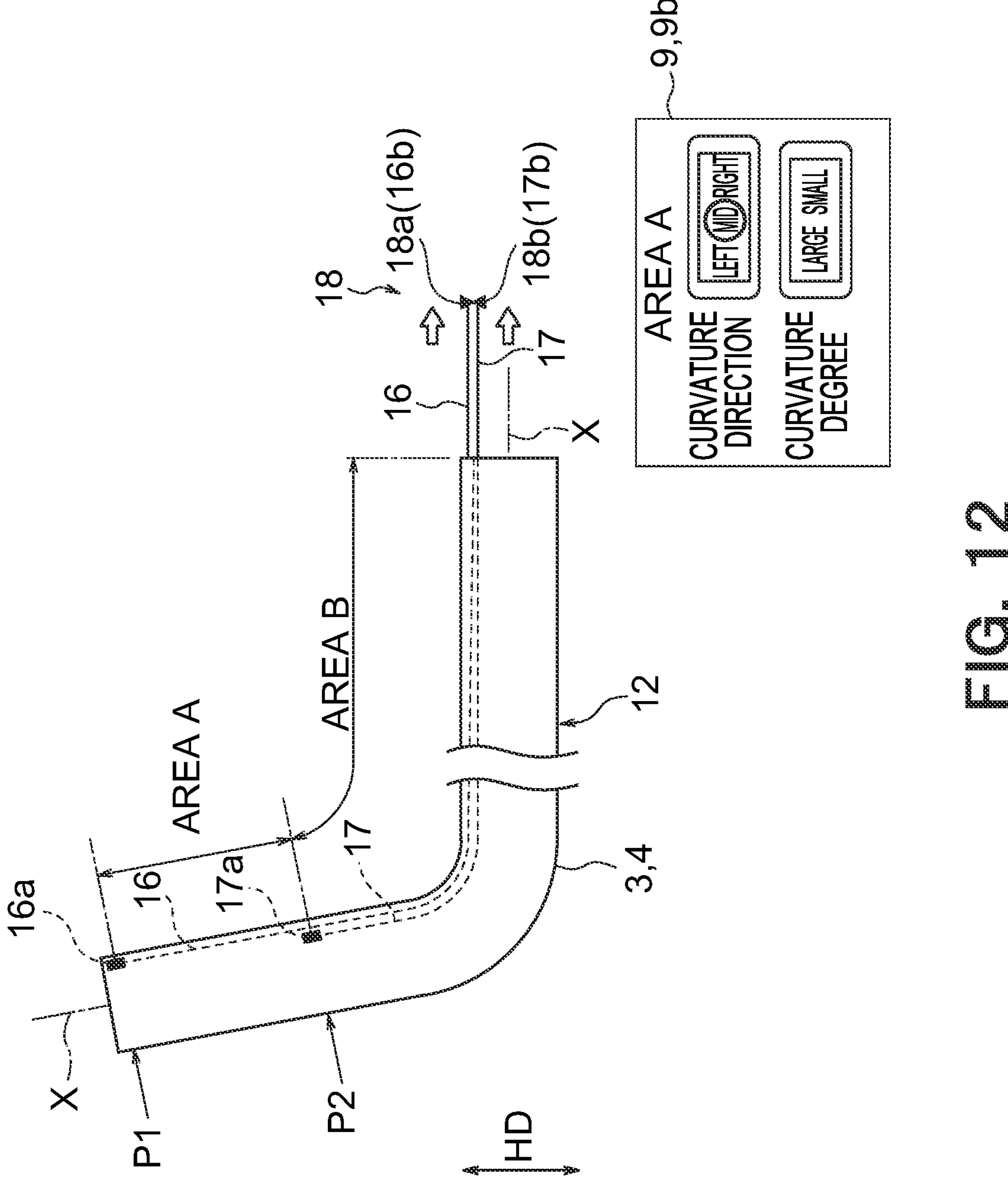
FIG. 12 is a view corresponding to FIG. 8, showing the base member with the curvature detection function which is curved rightward in the area B.

In addition, as shown in FIG. 12, when the base member 3 is curved rightward in the area B, the right side region of the area B (the region where the third linear member 16 and the fourth linear member 17 are disposed) is contracted due to the curvature. Thus, the second end 16*b* of the third linear member 16, which extends in the area B, moves with respect to the base member 3 to the one side (right side in FIG. 12) in the longitudinal direction LD. Similarly, the second end 17*b* of the fourth linear member 17, which extends in the area B, moves with respect to the base member 3 to the one side (right side in FIG. 12) in the longitudinal direction LD. A distance moved by the second end 17*b* of the fourth linear member 17 with respect to the base member 3 is the same as a distance moved by the second end 16*b* of the third linear member 16 with respect to the base member 3. As a result, the relative position between the second end 16*b* of the third linear member 16 and the second end 17*b* of the fourth linear member 17 does not change.

Therefore, it is possible to detect whether the base member 3 is curved in the area A by detecting change in a relative position between the second end 16*b* of the third linear member 16 and the second end 17*b* of the fourth linear member 17. In addition, it is possible to detect a direction of curvature (rightward or leftward) of the base member in the area A by detecting a direction of displacement of the second end 16*b* of the third linear member 16 with respect to the second end 17*b* of the fourth linear member 17.

In addition, when the base member 3 is curved in the area A, the amount of displacement of the second end 16*b* of the third linear member 16 with respect to the second end 17*b* of the fourth linear member 17 depends on a degree of the curvature of the area A (in other words, an angle of a direction in which the center axis X of the base member 3 at the fixed position P2 extends, with respect to a direction in which the center axis X of the base member 3 at the fixed position P1 extends). Thus, the degree of curvature of the base member 3 in the area A can be detected by detecting the amount of the displacement of the second end 16*b* with respect to the second end 17*b*.

Further, the direction of curvature of the base member 3 in the area A can be detected three-dimensionally by combining the detection result of curvature of the base member 3 obtained by the third linear member 16 and the fourth linear member 17, and the detection result of the curvature obtained by the first linear member 6 and the second linear member 7.

Next, a second distance displacement sensor 18 is described. The second distance displacement sensor 18 detects change in a relative position between the second ends 16*b*, 17*b* of the third linear member 16 and the fourth linear member 17. The second distance displacement sensor 18 includes a third sensor 18*a* and a fourth sensor 18*b*, and is capable of detecting change in a relative position between the third sensor 18*a* and the fourth sensor 18*b*. The third sensor 18*a* is fixed to the second end 16*b* of the third linear member 16, and the second sensor 18*b* is fixed to the second end 17*b* of the fourth linear member 17. The second distance displacement sensor 18 is electrically connected to the display device 9. When a relative position of the third sensor 18*a* with respect to the fourth sensor 18*b* changes, the second distance displacement sensor 18 inputs, to the display device 9, a signal corresponding to a direction and the amount of displacement of the third sensor 18*a* with respect to the fourth sensor 18*b*.

The display device 9 determines the direction and the degree of curvature of the base member 3 in the area A based on the signal inputted by the second distance displacement sensor 18, and displays them on a display 9*b*.

In the illustrated example, the display device 9 displays the curvature direction detected by the second distance displacement sensor 18 as "RIGHT," "MID" or "LEFT." Specifically, when the base member 3 is not curved in the area A as shown in FIGS. 8, 11 and 12, the display device 9 indicates the curvature direction as "MID." When the base member 3 is curved leftward in the area A as shown in FIG. 9, the display device 9 indicates the curvature direction as "LEFT." When the base member 3 is curved rightward in the area A as shown in FIG. 10, the display device 9 indicates the curvature direction as "RIGHT."

In addition, in the illustrated example, the display device 9 displays the curvature degree detected by the second distance displacement sensor 18 as "LARGE" or "SMALL." Specifically, when the amount of displacement of the third sensor 18*a* with respect to the fourth sensor 18*b* (thus the amount of displacement of the second end 16*b* of the third linear member 16 with respect to the second end 17*b* of the fourth linear member 17) is zero (this is the examples of FIGS. 8, 11 and 12), the display device 9 does not display the curvature degree. When the amount of displacement of the third sensor 18*a* with respect to the fourth sensor 18*b* is greater than 0 and less than a predetermined value, the display device 9 indicates the curvature degree as "SMALL." When the amount of displacement of the third sensor 18*a* with respect to the fourth sensor 18*b* is equal to or greater than the predetermined value, the display device 9 indicates the curvature degree as "LARGE."

Third Example

Next, a curvature detection system 101 according to a third example is described with reference to FIG. 13.

Figure 13:
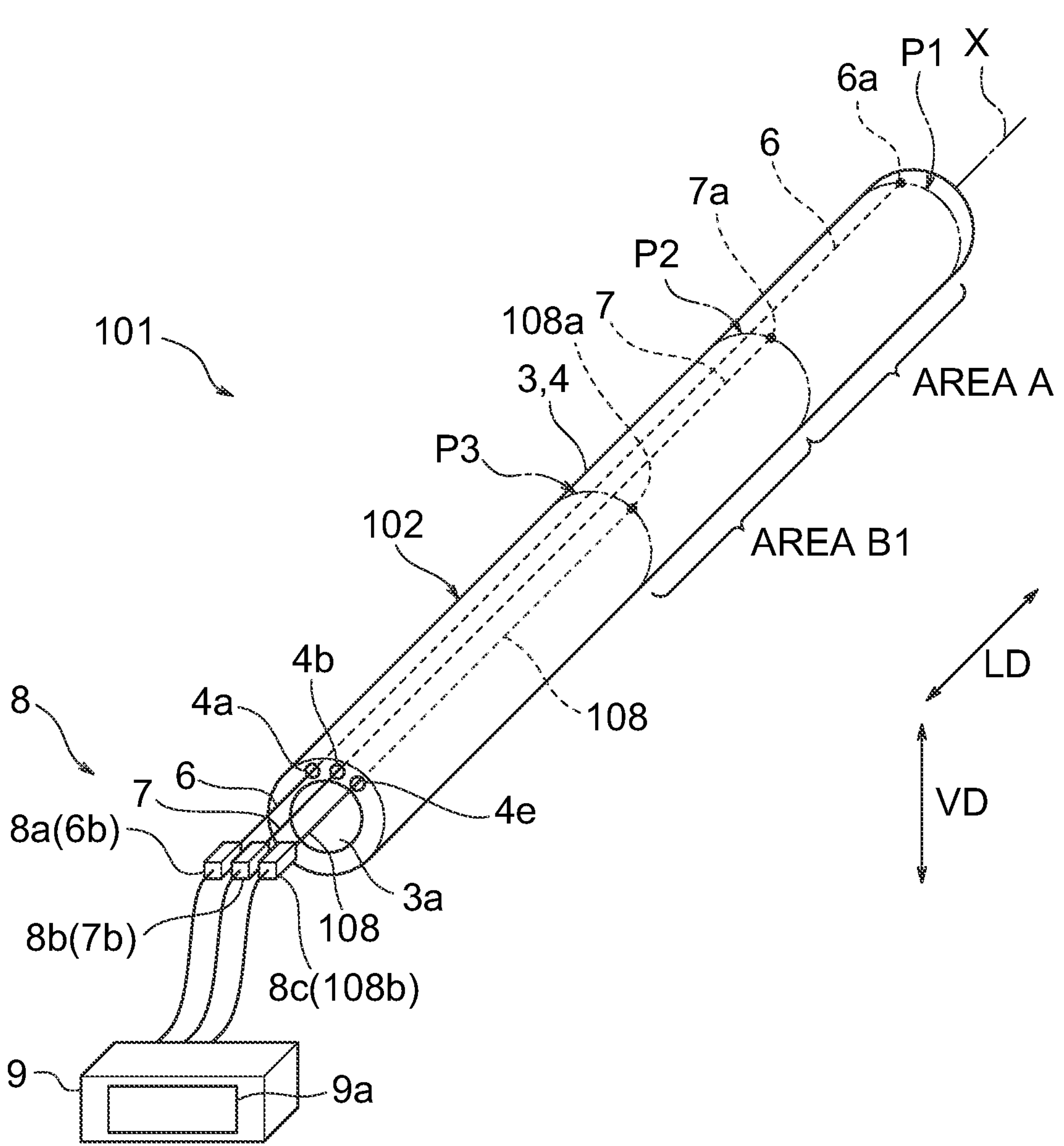
FIG. 13 is a view for describing a third example, and is a perspective view showing a base member with a curvature detection function and a curvature detection system.

An example shown in FIG. 13 differs from the curvature detection system 1 shown in FIGS. 1 to 6 in that a base member with a curvature detection function 102 further has a fifth linear member 108 that extends adjacently to a first linear member 6 and a second linear member 7 in a longitudinal direction LD, and that a distance displacement sensor 8 further has a fifth sensor 8*c*. Other configurations are substantially the same as those of the curvature detection system 1 shown in FIGS. 1 to 6. In the example shown in FIG. 13, the same numerals are given to the same parts as those of the first example shown in FIGS. 1 to 6, and detailed description thereof is omitted.

In the example shown in FIG. 13, a base member 3 further has a fifth lumen 4*e* which extends adjacently to a first lumen 4*a* and a second lumen 4*b* in the longitudinal direction LD. The fifth lumen 4*e* is formed in a wall 4 of the base member 3.

A fifth linear member 108 is disposed in the fifth lumen 4*e*. Since the fifth linear member 108 is disposed in the lumen 4*e*, the risk of damaging the fifth linear member 108 is reduced. In addition, since the linear members 6, 7, 108 are disposed in the lumens 4*a*, 4*b*, 4*e* separated from one another, the risk of causing the linear members 6, 7, 108 to be entangled is reduced.

The fifth linear member 108 has a first end 108*a* and a second end 108*b* positioned on one side of the first end 108*a* in the longitudinal direction LD. The first end 108*a* of the fifth linear member 108 is fixed to a third fixed position P3 of the base member 3 in the fifth lumen 4*e*. The rest part of the fifth linear member 108, which includes the second end 108*b*, is disposed in the fifth lumen 4*e* so that the rest part is relatively movable with respect to the base member 3, as well as the first linear member 6 and the second linear member 7, in the longitudinal direction LD. The third fixed position P3 is located at a position apart from the first fixed position P1 and the second fixed position P2 in the longitudinal direction LD. In the illustrated example, the third fixed position P3 is located on the one side of the second fixed poison P2 in the longitudinal direction LD.

The fifth linear member 108 is made of a low-stretch material compared to the base member 3 and can be curved along the base member 3 when it is curved. Similarly to the first linear member 6 and the second linear member 7, the fifth linear member 108 can be made of various materials such as metal, resin or the like, depending on an application of the base member with the curvature detection function 102. The fifth linear member 108 is preferably made of the same material as that of the first linear member 6 and the second linear member 7.

In the illustrated example, a length of the fifth linear member 108 is determined such that, as shown in FIG. 13, the second end 108*b* of the fifth linear member 108 is located at the same position as the second end 6*b* of the first linear member 6 and the second end 7*b* of the second linear member 7 in the longitudinal direction LD, with the base member 3 not curved at any position in the longitudinal direction LD. However, as described later, this disclosure is not limited to this example, as long as it is possible to detect change in a relative position between the second end 6*b* of the second linear member 6 and the second end 108*b* of the fifth linear member 108.

The base member with the curvature detection function 102 as structured above can detect curvature of the base member 3 between the first fixed position P1 and the second fixed position P2, based on change in a relative position between the second ends 6*b*, 7*b* of the first linear member 6 and the second linear member 7. Further, the base member with the curvature detection function 102 can detect curvature of the base member 3 in an area B1 between the second fixed position P2 and the third fixed position P3, based on change in a relative position between the second ends 7*b*, 108*b* of the second linear member 7 and the fifth linear member 108.

Next, the distance displacement sensor 8 in the third example is described. As described above, the distance displacement sensor 8 in this example has the fifth sensor 8*c* in addition to a first sensor 8*a* and a second sensor 8*b*. The fifth sensor 8*c* is fixed to the second end 108*b* of the fifth linear member 108. The distance displacement sensor 8 in this example is capable of detecting change in a relative position between the second sensor 8*b* and the fifth sensor 8*c*, in addition to change in a relative position between the first sensor 8*a* and the second sensor 8*b*. When a relative position of the first sensor 8*a* with respect to the second sensor 8*b* changes, the distance displacement sensor 8 in this example inputs, to a display device 9, a signal corresponding to a direction and the amount of displacement of the first sensor 8*a* with respect to the second sensor 8*b*. Further, when a relative position of the second sensor 8*b* with respect to the fifth sensor 8*c* changes, the distance displacement sensor 8 in this example inputs, to the display device 9, a signal corresponding to a direction and the amount of displacement of the second sensor 8*b* with respect to the fifth sensor 8*c*.

The display device 9 determines the directions and the degrees of curvature of the base member 3 in the area A and the area B1 based on the signals inputted by the distance displacement sensor 8, and displays them on a display 9*a*.

Example of Application to Balloon Catheter

Figure 14:
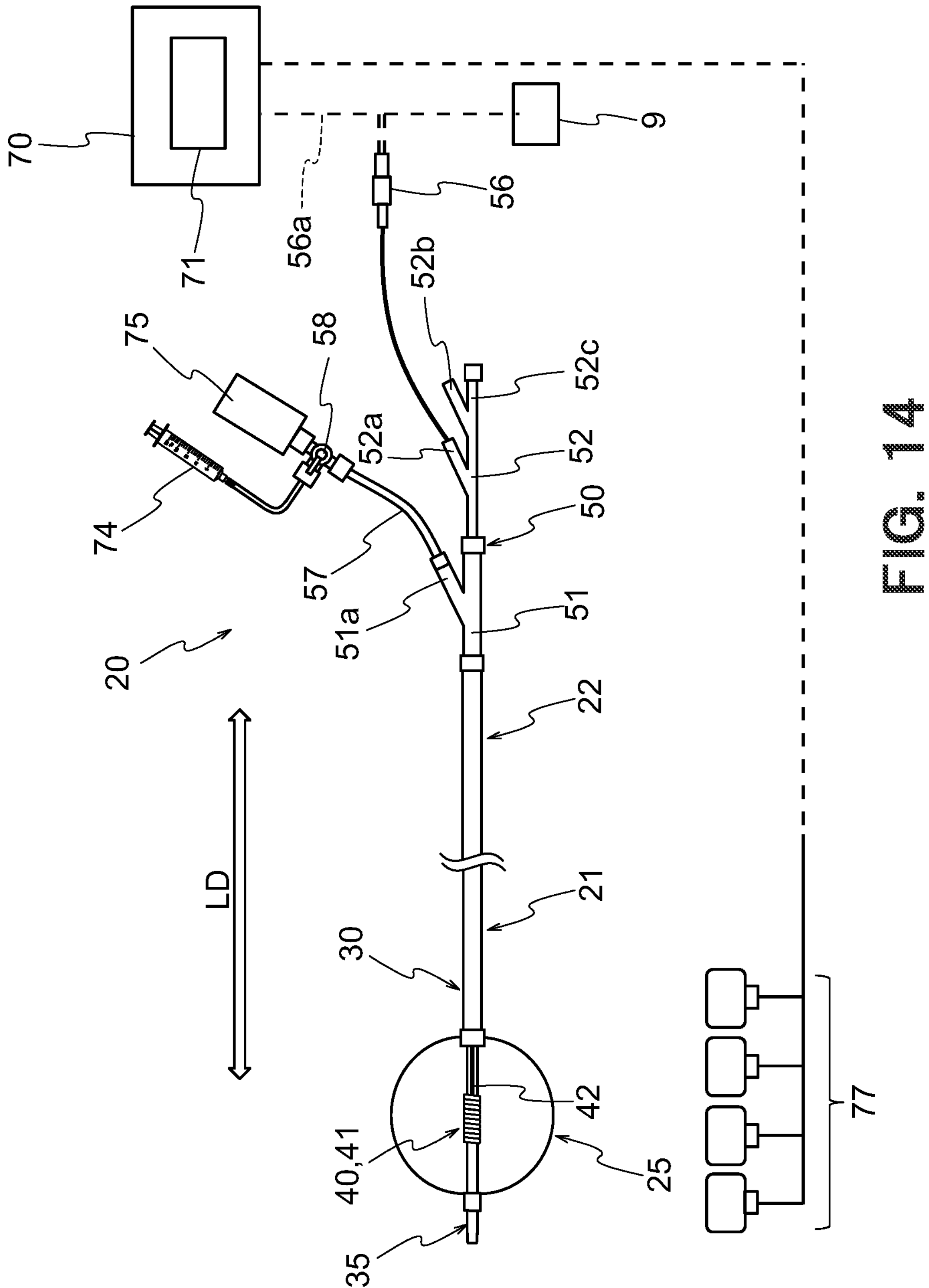
FIG. 14 is a view for describing an example of application of the base member with the curvature detection function and the curvature detection system, showing a balloon catheter and a balloon catheter system.

Next, an example of application of the aforementioned curvature detection system to a balloon catheter is described. A balloon catheter to which the curvature detection system in the second example is applied is particularly described herein. FIG. 14 is a view showing an entire structure of the catheter system including the balloon catheter.

A balloon catheter system 20 shown in FIG. 14 has a balloon catheter 21, and a heating device 70, a supply device 74 and an agitation device 75 which are connected to the balloon catheter 21. The balloon catheter 21 has a catheter body 22 having a longitudinal direction LD, and a handle 50 connected to a proximal end of the catheter body 22.

Figure 15:
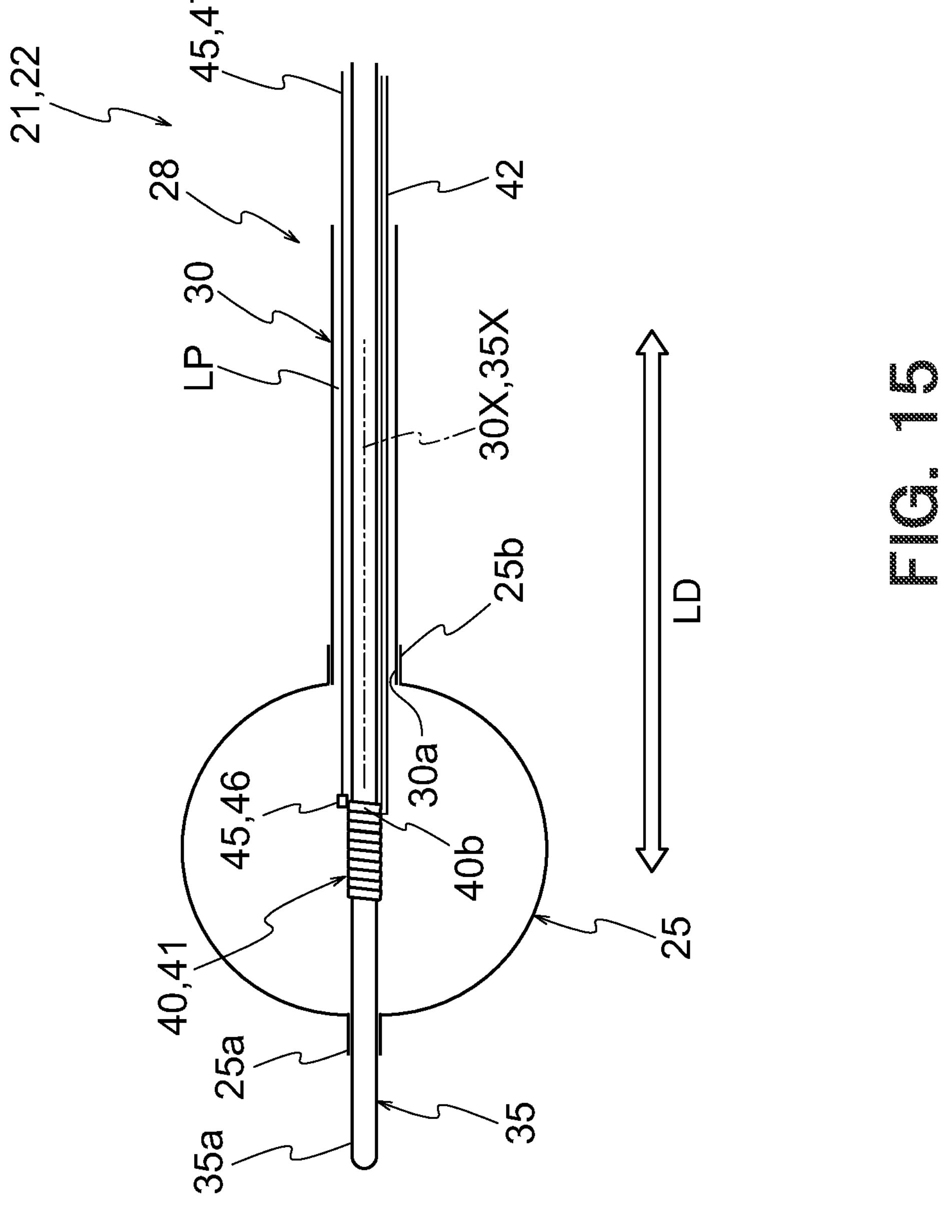
FIG. 15 is a view showing a distal end portion of the balloon catheter of FIG. 14, with a balloon inflated.

As shown in FIG. 15, the catheter body 22 in this application example has a balloon 25, an outer cylinder shaft 30 connected to a proximal end 25*b* of the balloon 25, an inner cylinder shaft 35 connected to a distal end 25*a* of the balloon 25, and a heating member 40 disposed in the balloon 25. The inner cylinder shaft 35 extends inside the outer cylinder shaft 30 and into the balloon 25. A liquid delivery path LP in communication with an inside of the balloon 25 is formed between the outer cylinder shaft 30 and the inner cylinder shaft 35. The heating member 40 is for heating a liquid in the balloon 25.

The longitudinal direction LD of the catheter body 22 is specified as a direction along which center axes 30X, 35X of the outer cylinder shaft 30 and the inner cylinder shaft 35 extending from the outer cylinder shaft 30 extend. The term "distal" side used for respective components of the balloon catheter 21 and the catheter body 22 means a side distant from an operator (surgeon) operating the handle 50 and the balloon catheter 21 along the longitudinal direction LD of the catheter body 22, in other words, a distant side. In addition, the term "proximal" side used for respective components of the balloon catheter 21 and the catheter body 22 means a side close to the operator (surgeon) operating the handle 50 and the balloon catheter 21 along the longitudinal direction LD of the catheter body 22, in other words, a near side.

The balloon catheter 21 is further described in detail below. The catheter body 22 of the balloon catheter 21 is first described in detail. As described above, the catheter body 22 of the balloon catheter according to this example has the balloon 25, the outer cylinder shaft 30, the inner cylinder shaft 35, and the heating member 40. Further, the catheter body 22 in this example has a temperature sensor 45 disposed in an inside space of the balloon 25.

The outer cylinder shaft 30 and the inner cylinder shaft 35 both have a tubular shape, typically a cylindrical shape. Thus, the outer cylinder shaft 30 and the inner cylinder shaft 35 respectively form lumens as inside spaces. A not-shown guide wire, for example, is inserted thorough the lumen formed by the inner cylinder shaft 35. The inner cylinder shaft 35 is inserted through the lumen formed by the outer cylinder shaft 30. Namely, the outer cylinder shaft 30 and the inner cylinder shaft 35 form a dual shaft structure. An internal diameter of the outer cylinder shaft 30 is larger than an external diameter of the inner cylinder shaft 35. Thus, a lumen remains between the outer cylinder shaft 30 and the inner cylinder shaft 35. The lumen between the outer cylinder shaft 30 and the inner cylinder shaft 35 forms the liquid delivery path LP. As shown in FIG. 15, the liquid delivery path LP is in communication with the inside of the balloon 25. The liquid delivery path LP extends into the handle 50.

Lengths of the outer cylinder shaft 30 and the inner cylinder shaft 35 are preferably between 500 mm or more and 1700 mm or less, and more preferably between 600 mm or more and 1200 mm or less. The outer cylinder shaft 30 and the inner cylinder shaft 35 are preferably made of a flexible material with excellent antithrombotic properties. The flexible material with excellent antithrombotic properties may include, for example, fluoropolymers, polyamides, polyurethane-based polymers, or polyimides, but is not limited thereto. The outer cylinder shaft 30 is preferably manufactured by stacking layers of different flexible materials to have both sliding facility to the inner cylinder shaft 35 and adhesion or heat weldability to the balloon 25.

The external diameter of the outer cylinder shaft 30 is preferably between 3.0 mm or more and 5.0 mm or less. The internal diameter of the outer cylinder shaft 30 is preferably between 2.0 mm or more and 4.0 mm or less. The external diameter of the inner cylinder shaft 35 is preferably between 1.0 mm or more and 3.0 mm or less. The internal diameter of the inner cylinder shaft 35 is preferably between 0.5 mm or more and 2.0 mm or less.

The balloon 25 is connected to the outer cylinder shaft 30 and the inner cylinder shaft 35. The balloon 25 is formed to be inflatable when it is filled with a liquid and deflatable when the liquid is discharged therefrom. The balloon 25 is preferably shaped to fit a target site to be treated (e.g., blood vessel). As an example, the balloon 25 adapted for a pulmonary vein junction of a left atrium may have a spherical shape having a diameter between 15 mm or more and 40 mm or less. The spherical shape here includes a true spherical shape, a prolate shape, and a prolate spheroid shape. It also includes a substantially spherical shape.

A thickness of the balloon 25 is preferably between 20 μm or more and 100 μm or less. A material of the balloon 25 is preferably an elastic material with excellent antithrombotic properties such as a polyurethane-based polymer material. The polyurethane-based polymer material applicable to the balloon 25 may be, for example, thermoplastic polyether urethane, polyether polyurethane urea, fluorinated polyether urethane urea, polyether polyurethane urea resin, or polyether polyurethane urea amide.

In the illustrated catheter body 22, as shown in FIGS. 14 and 15, the distal end (distant end) 25*a* of the balloon 25 is fixed to a distal end (distant end) 35*a* of the inner cylinder shaft 35. The proximal end (near end) 25*b* of the balloon 25 is fixed to a distal end (distant end) 30*a* of the outer cylinder shaft 30. In the illustrated example, the distal end 30*a* of the outer cylinder shaft 30 does not extend into the balloon 25. However, not limited to the illustrated example, the distal end 30*a* of the outer cylinder shaft 30 may extend into the balloon 25. The balloon 25 may be connected to the outer cylinder shaft 30 and the inner cylinder shaft 35 by adhesion or heat welding.

Figure 16:
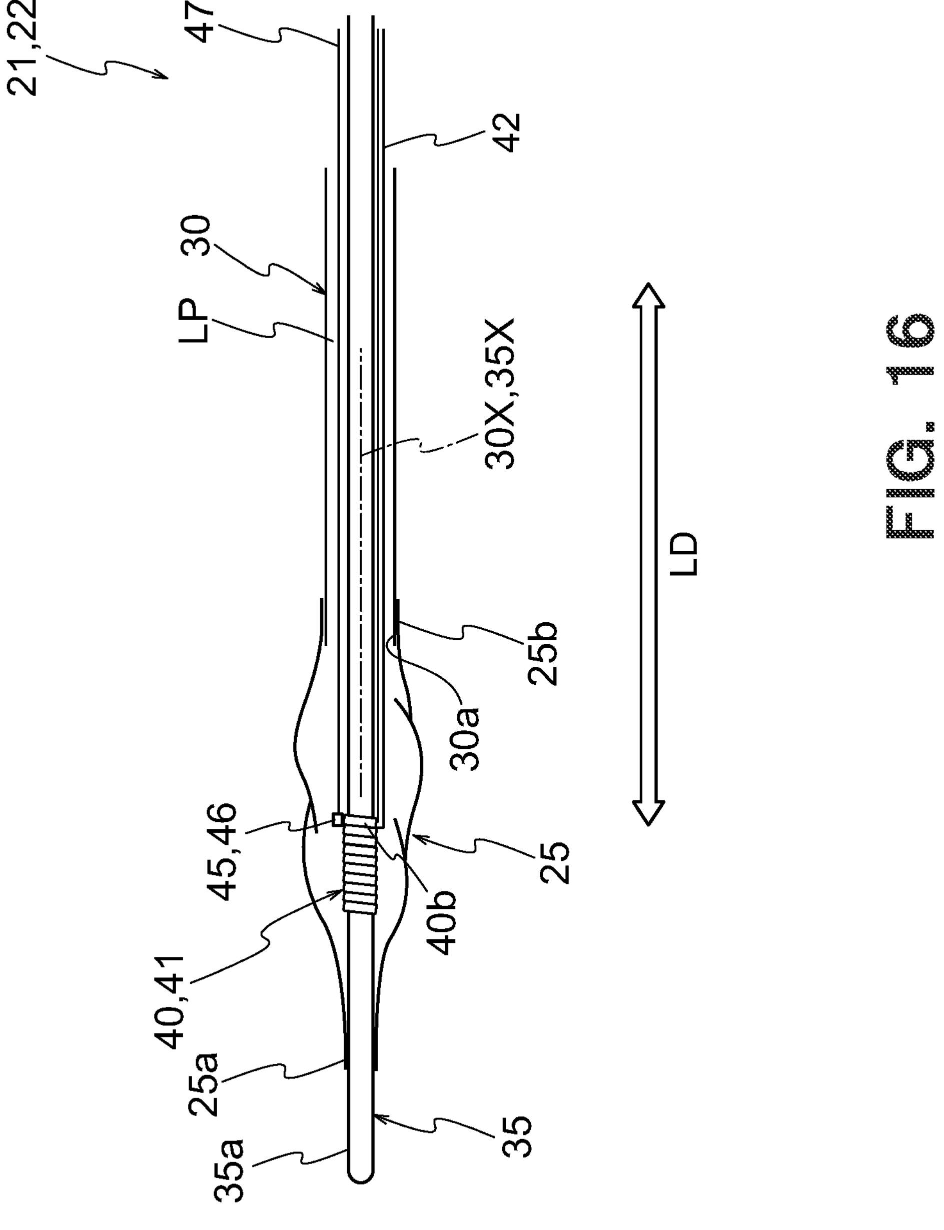
FIG. 16 is a view showing the distal end portion of the balloon catheter of FIG. 14, with the balloon deflated and stretched.

By the relative movement between the outer cylinder shaft 30 and the inner cylinder shaft 35 in the longitudinal direction LD, the balloon 25 connected to the outer cylinder shaft 30 and the inner cylinder shaft 35 deforms. In the illustrated example, the relative movement between the outer cylinder shaft 30 and the inner cylinder shaft 35 allows a dimension of the balloon 25 to be adjusted in the longitudinal direction LD. As shown in FIG. 16, when the inner cylinder shaft 35 is relatively moved with respect to the outer cylinder shaft 30 to the distal side in the longitudinal direction LD, the balloon 25 is stretched in the longitudinal direction LD and is strained. In the illustrated example, the movement range of the inner cylinder shaft 35 with respect to the outer cylinder shaft 30 to the distal side in the longitudinal direction LD is restricted by the balloon 25. When the inner cylinder shaft 35 in the state shown in FIG. 16 is relatively moved with respect to the outer cylinder shaft 30 to the proximal side in the longitudinal direction LD, the balloon 25 becomes loosened. By introducing a liquid into the loosened balloon 25, the balloon 25 can be inflated as shown in FIG. 15. Namely, the relative movement between the outer cylinder shaft 30 and the inner cylinder shaft 35 allows the dimension of the balloon 25 to be adjusted in the longitudinal direction LD.

Next, the heating member 40 is described. The heating member 40 is disposed in the balloon 25. The heating member 40 is a member for heating a liquid filled in the balloon 25. As an example, a nichrome wire that generates electric resistance heat can be employed as the heating member 40. A coil electrode 41 may be employed as another example of the heating member 40, as shown in FIGS. 15 and 16. By high-frequency current conduction (high-frequency energization) to the heating member 40 as the coil electrode 41, a high-frequency current flows between the coil electrode 41 and a counter electrode 77 (FIG. 14) disposed outside so that the liquid positioned between the coil electrode 41 and the counter electrode 77 generates Joule heat. The counter electrode 77 is located on the back of a patient, for example.

In the example shown in FIGS. 15 and 16, the coil electrode 41 is provided on the inner cylinder shaft 35 extending inside the balloon 25. The coil electrode 41 may be made by a conductive wire wound around the inner cylinder shaft 35. The coil electrode 41 is electrically connected to a wire 42 for high-frequency current conduction. The wire 42 extends in the liquid delivery path LP, which is a lumen between the outer cylinder shaft 30 and the inner cylinder shaft 35, to the handle 50. A specific example of the coil electrode 41 forming the heating member 40 may be a coil electrode that is made as follows. An insulation-coated lead wire used as the wire 42 is stripped of its coating. Then, the lead wire is wound around the inner cylinder shaft 35 to provide a coil electrode. Since such a coil electrode 41 is integrally formed with the wire 42, occurrence of trouble such as disconnection of wire can be effectively minimized.

Diameters of the coil electrode 41 and the wire 42 are preferably between 0.1 mm or more and 1 mm or less, and more preferably between 0.1 mm or more and 0.4 mm or less. A conductive material forming the coil electrode 41 and the wire 42 may be, for example, copper, silver, gold, platinum, and alloys thereof. To prevent a short circuit, the wire 42 is preferably a conductive linear member covered with an insulating film made of fluoropolymer, for example.

Next, the temperature sensor 45 is described. The temperature sensor 45 is disposed in the inside space of the balloon to acquire information on a temperature of a liquid in the balloon 25. In the illustrated example, the temperature sensor 45 has a thermosensitive part 46 disposed in the vicinity of the heating member 40. The temperature sensor 45 can acquire information of a temperature of a liquid in the vicinity of the heating member 40. The liquid around the heating member 40 can be heated to a proper temperature by applying electric energy to the heating member 40 based on the information acquired by the temperature sensor 45.

A thermocouple or thermistor can be used as the temperature sensor 45. Information on a temperature acquired by the temperature sensor 45 is, for example, an electric potential that can be acquired from a thermocouple, or a resistance value that can be acquired from a thermistor.

As shown in FIGS. 15 and 16, the temperature sensor 45 typically has the thermosensitive part 46, and a lead wire 47 electrically connected to the thermosensitive part 46. When the temperature sensor 45 comprises a thermocouple, a part where different metals are connected in the thermocouple serves as the thermosensitive part 46. When the temperature sensor 45 comprises a thermistor, a ceramic element in the thermistor serves as the thermosensitive part 46. The lead wire 47 extends inside the liquid delivery path LP, which is the lumen between the outer cylinder shaft 30 and the inner cylinder shaft 35, to the handle 50.

A diameter of the lead wire 47 is preferably between 0.05 mm or more and 0.5 mm or less, and more preferably between 0.05 mm or more and 0.3 mm or less. The temperature sensor 45 comprising a thermocouple may be formed by using constantan for the lead wire 47 and copper for the wire 42 for high-frequency current conduction, and by joining them. In this example, the thermosensitive part 46 formed by joining the lead wire 47 and the wire 42 can function as a thermocouple. To prevent a short circuit between the lead wire 47 and the wire 42, the lead wire 47 is preferably provided with an electrically insulating cover made of fluoropolymer, enamel or the like.

Next, the handle 50 connected to the aforementioned catheter body 22 from the proximal side is described. The handle 50 is a part grasped by an operator (surgeon) during the use of the balloon catheter system 20. Thus, the handle 50 preferably has a design that allows an operator to easily grasp and operate the handle 50 with his/her hand. The handle 50 is preferably made of a material having excellent chemical resistance such as polycarbonate or ABS resin.

The handle 50 shown in FIG. 14 has a first handle part 51 and a second handle part 52 that are slidable to each other. The first handle part (front handle part) 51 is connected to the outer cylinder shaft 30 of the catheter body 22. The second handle part (rear handle part) 52 is connected to the inner cylinder shaft 35 of the catheter body 22. By relatively moving the second handle part 52 with respect to the first handle part 51, the inner cylinder shaft 35 can be relatively moved with respect to the outer cylinder shaft 30.

As shown in FIG. 14, the handle 50 also functions as a part that connects devices included in the balloon catheter system 20, and the balloon catheter 21.

A connector 56 extends from the second handle part 52. The connector 56 electrically connects the wire 42 and the lead wire 47 to the external heating device 70. The connector 56 extends from one branch 52*a* of a plurality of branches 52*a*, 52*b*, 52*c* of the second handle part 52.

The connector 56 preferably has a structure capable of effectively preventing improper connection. In addition, the connector 56 preferably has excellent waterproofness. The structure of the connector 56 can be decided in consideration of surgeon's convenience and design matter. Similarly to the handle 50, the connector 56 is preferably made of a material forming having excellent chemical resistance such as polycarbonate or ABS resin.

The connector 56 may have therein a highly conductive metal pin. The wire 42 and the lead wire 47 are connected to this highly conductive metal pin to be electrically connectable to the heating device 70 serving as means for supplying high-frequency power. The lead wire 47 may be electrically connected to a device other than the heating device 70 serving as means for supplying high-frequency power such as a temperature indicator. A material of the highly conductive metal pin included in the connector 56 may be of any type as long as it is a metal having high conductivity. A material of the high conductive metal pin included in the connector 56 may be, for example, copper, silver, gold, platinum, and alloys thereof. In addition, an outside of the highly conductive metal pin is preferably protected by a material having electrically insulating properties and chemical resistance. An electrically insulating and chemically resistant material may be, for example, polysulfone, polyurethane-based polymers, polypropylene, or polyvinyl chloride.

The second handle part 52 has branches 52*b* and 52*c* other than the branch 52*a* to which the connector 56 is connected. These branches 52*b* and 52*c* serve as a part through which a liquid is supplied to the lumen as an inside space of the inner cylinder shaft 35, and a part from which a guide wire inserted through the lumen of the inner cylinder shaft 35 extends. During a cardiac ablation therapy, a saline solution the amount of which is as small as about 100 ml/hour is generally injected into a patient's body through the lumen of the inner cylinder shaft 35. The injection of saline solution effectively prevents backflow of blood into the lumen of the inner cylinder shaft 35.

In addition, as shown in FIG. 14, an extension tube 57 extends from the first handle part 51. The extension tube 57 communicates the liquid delivery path LP of the catheter body 22 with an external supply device 74 or the external agitation device 75. The extension tube 57 extends from the branch 51*a* provided on the first handle part 51. The extension tube 57 is connected to the supply device 74 and the agitation device 75 via a valve 58. In the illustrated example, whether the supply device 74 or the agitation device 75 is communicated with the liquid delivery path LP can be selected by operating the valve 58. A three-way stopcock may be used as the valve 58.

Next, devices constituting the balloon catheter system 20 together with the aforementioned balloon catheter 21, to be specific, the heating device 70, the supply device 74 and the agitation device 75, are described.

The illustrated heating device 70 is electrically connected to the coil electrode 41 via a connection cable 56*a* and the wire 42. High-frequency power generated by the heating device 70 is supplied to the coil electrode 41 through the connection cable 56*a* and the wire 42. The heating device 70 has a high-frequency current conduction controller 71 that controls high-frequency current conduction to the coil electrode 41. In the illustrated example, the high-frequency current conduction controller 71 controls the high-frequency current conduction to the coil electrode 41 to adjust an output from the heating member 40. The high-frequency current conduction controller 71 is electrically connected to the connection cable 56*a* and the lead wire 47 to be capable of controlling the high-frequency current conduction to the coil electrode 41 based on information on a temperature of a liquid in the balloon 25, which is acquired by the temperature sensor 45.

The heating device 70 is constituted of hardware such as a CPU, for example. One or more of the high-frequency current conduction controller 71 and another component included in the heating device 70 may be constituted by a separate hardware. At least a part of the heating device 70 may be constituted by a software. A part of the heating device 70 may be physically separated from the other part of the heating device 70. A component of the heating device 70 may be able to cooperate with another component thereof by communication through a network. A component of the heating device 70 may be on a device such as a server or database in the cloud, which can communicate with another component of the heating device 70 through an external network.

Next, the supply device 74 is described. The supply device 74 supplies a liquid into the liquid delivery path LP. The supply device 74 can inflate the balloon 25, as shown in FIG. 15, by supplying a liquid to the balloon 25 through the liquid delivery path LP. Also, the supply device 74 can deflate the balloon 25 by discharging the liquid from the balloon 25 through the liquid delivery path LP. A syringe can be used as the supply device 74 as illustrated. A pump or the like can also be used as the supply device 74. The liquid to be supplied to the liquid delivery path LP is preferably a contrast or a contrast diluted with saline in order that the balloon 25 inflated with the liquid can be seen in a radiographic image.

Next, the agitation device 75 is described. The agitation device 75 is provided for agitating a liquid in the balloon 25. By agitating the liquid in the balloon 25, the liquid heated by the heating member 40 can be diffused to equalize a temperature of the liquid in the balloon 25. As a result, a surface temperature of the balloon 25 can be adjusted. The agitation device 75 repeats supply of liquid to the liquid delivery path LP and discharge of liquid from the liquid delivery path LP. Thus, supply of liquid from the liquid delivery path LP into the balloon 25 and discharge of liquid from inside the balloon 25 to the liquid delivery path LP are repeated so that the liquid in the balloon 25 is agitated. A pump selected from the group consisting of a roller pump, a diaphragm pump, a bellows pump, a vane pump, a centrifugal pump, and a pump comprising a piston and a cylinder in combination, can be employed as the agitation device 75.

The amount of liquid to be supplied to the liquid delivery path LP and the amount of liquid to be discharged from the liquid deliver path LP may be a predetermined amount (e.g., between 0.5 ml or more and 1.5 ml or less). Supply of liquid to the liquid delivery path LP and discharge of liquid from the liquid delivery path LP may be repeated at a regular cycle (e.g., between once or more and three times or less per second). The amount of liquid to be supplied to the liquid delivery path LP and the amount of liquid to be discharged from the liquid deliver path LP may be adjusted by a control signal from a not-shown agitation-device controller or by a direct input from an operator. Similarly, a cycle at which a liquid is supplied to the liquid delivery path LP and a liquid is discharged from the liquid delivery path LP may be adjusted by a control signal from the not-shown agitation-device controller or by a direct input from an operator.

To adjust a surface temperature of the balloon 25 to an ideal temperature, it is necessary to efficiently diffuse a liquid heated by the heating member 40 in the balloon 25. To diffuse the heated liquid efficiently, most (or all) of the liquid flowing from the liquid delivery path LP into the balloon 25 is desired to be directed to the heating member 40, during the supply of liquid by the agitation device 75 from the liquid delivery path LP into the balloon 25. However, if a pressing force is applied to the balloon 25, for example so that the inner cylinder shaft 35 is curved during an operation, there is a possibility that a direction along which the distal end 30*a* of the outer cylinder shaft 30 and the heating member 40 are aligned is significantly displaced from an ejection direction along which the liquid is ejected from the distal end 30*a* of the outer cylinder shaft 30 (a direction along the center axis 30X of the outer cylinder shaft 30 at the distal end 30*a*). When the liquid is supplied into the balloon 25 under this state, most or all of the liquid flowing from the liquid delivery path LP into the balloon 25 is not directed to the heating member 40 so that most or all of the heated liquid close to the heating member 40 cannot be diffused. As a result, a surface temperature of the balloon 25 cannot be increased as desired. In addition, since a temperature of the liquid in the vicinity of the temperature sensor 45 is maintained to be high, electric energy is not sufficiently supplied from the heating device 70 to the heating member 40 although a surface temperature of the balloon 25 has not risen to a desired temperature. Also, in this example, there is a possibility that a surface temperature of the balloon 25 cannot be raised as desired. Namely, unless the liquid heated by the heating member 40 can be efficiently diffused, it is difficult to adjust a surface temperature of the balloon 25 to an ideal temperature.

Figure 19:
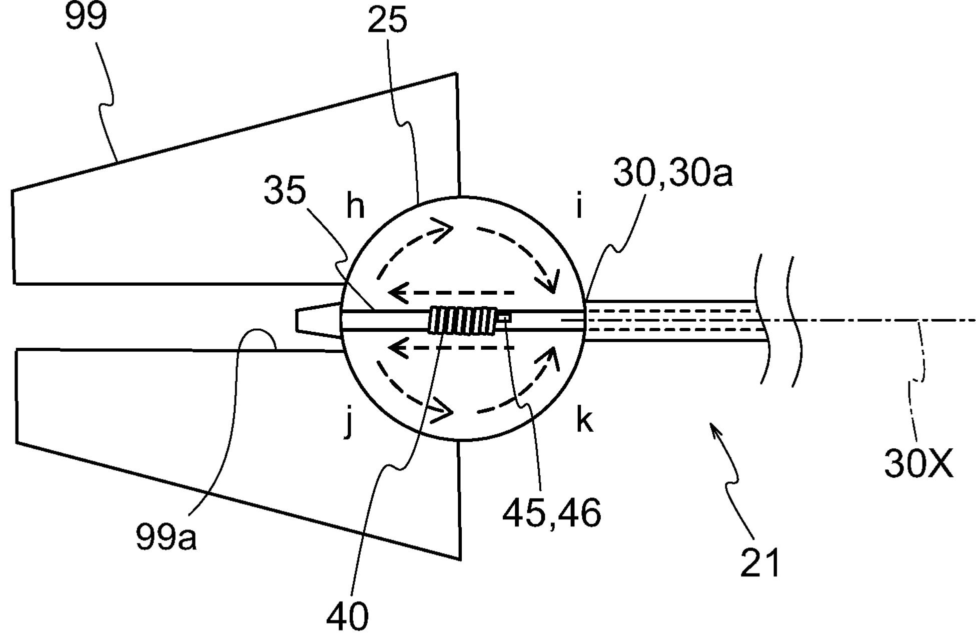
FIG. 19 is a view showing a conventional balloon catheter pressed against an ostia venarum pulmonalium.

FIG. 19 shows the balloon catheter 21, with the balloon 25 being perpendicularly pressed against an opening surface of an ostia venarum pulmonalium 99*a* of a pseudo-living body 99. In the example shown in FIG. 19, a direction along which the force is applied to the balloon 25 is a direction along the center axis 30X at the distal end 30*a* of the outer cylinder shaft 30. The inner cylinder shaft 35 is not curved between the distal end 30*a* of the outer cylinder shaft 30 and the heating member 40. Thus, the distal end 30*a* of the outer cylinder shaft 30 and the heating member 40 are aligned along the ejection direction (the direction along the center axis 30X of the outer cylinder shaft 30 at the distal end 30*a*) along which the liquid is ejected from the distal end 30*a* of the outer cylinder shaft 30.

Figure 20:
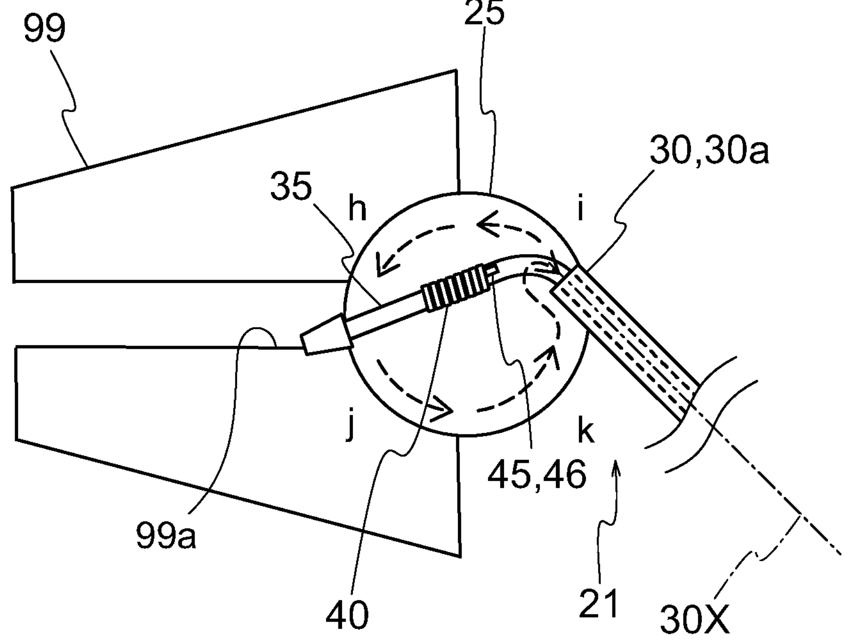
FIG. 20 is a view showing a conventional balloon catheter pressed against an ostia venarum pulmonalium.

FIG. 20 shows the balloon catheter 21, with the balloon 25 being pressed against the opening surface of the ostia venarum pulmonalium 99*a* of the pseudo-living body 99 at an angle between 45 degrees and 60 degrees. In the example shown in FIG. 20, a direction along which the force is applied to the balloon 25 intersects the direction along the center axis 30X at the distal end 30*a* of the outer cylinder shaft 30. The inner cylinder shaft 35 is largely curved between the distal end 30*a* of the outer cylinder shaft 30 and the heating member 40. Thus, the distal end 30*a* of the outer cylinder shaft 30 and the heating member 40 are not aligned along the ejection direction, along which the liquid is ejected from the distal end 30*a* of the outer cylinder shaft 30.

In FIGS. 19 and 20, a flow of the liquid (agitation flow) ejected from the distal end 30*a* of the outer cylinder shaft 30 into the balloon 25 is indicated by arrows.

As can be understood from FIG. 19, when the inner cylinder shaft 35 is not curved between the distal end 30*a* of the outer cylinder shaft 30 and the heating member 40, a large part of the liquid ejected from the liquid delivery path LP into the balloon 25 surrounds the inner cylinder shaft 35 moving toward the heating member 40. Then, the liquid surrounds the heating member 40 anew diffusing a large part of the heated liquid in the vicinity of the heating member 40. The diffused liquid moves toward the surface of the balloon 25 to heat the surface of the balloon 25. The liquid which has surrounded the heating member 40 anew is heated by the heating member 40. In the example shown in FIG. 19, the liquid heated by the heating member 40 is evenly diffused in the balloon 25, whereby the inside of the balloon 25 and the surface of the balloon 25, i.e., areas indicated by h, i, j, k in FIG. 19 have substantially the same temperature as a whole. In addition, since the liquid heated by the heating member 40 is efficiently diffused, it is easy to adjust a surface temperature of the balloon 25 to a desired temperature by adjusting supply of electric energy to the heating member 40. This can significantly improve an ablation therapy effectiveness.

On the other hand, as can be understood from FIG. 20, when the inner cylinder shaft 35 is largely curved between the distal end 30*a* of the outer cylinder shaft 30 and the heating member 40, the liquid ejected from the liquid delivery path LP into the balloon 25 is deflected from the heating member 40 and moves toward the surface of the balloon 25 without being heated by the heating member 40. Thus, the liquid heated by the heating member 40 cannot be efficiently diffused. Specifically, most (or all) of the liquid heated by the heating member 40 cannot be diffused by the agitation flow. Alternatively, the heated liquid cannot be evenly diffused in the balloon 25. As a result, conduction of heat generated by the heating member 40 relies on thermal radiation in the balloon 25, which makes the temperature of the entire balloon 25 low and unstable. Alternatively, the surface temperature of the balloon 25 becomes uneven. For example, when the liquid flows in the balloon 25 as shown in FIG. 20, temperatures of surface areas indicated by i and h may be lower than those of areas indicated by j and k. This makes it difficult to adjust a surface temperature of the balloon 25 to a desired temperature. As a result, an ablation therapy canton be performed as desired.

In general, a balloon catheter is operated observing a radioscopic image of a distant end of the balloon catheter. The radioscopic image is a two-dimensional image. Thus, it is difficult to perceive curvature of the distant end of the balloon catheter based on the radioscopic image. Even when curvature is perceived, it is difficult to find out a direction and/or a degree of the curvature. To make it possible to perceive a direction and a degree of curvature of a balloon catheter during an operation on a constant basis, it is generally necessary to obtain radioscopic images as video images. However, this solution is problematic in that it increases the amount of X-ray exposure.

Figure 17:
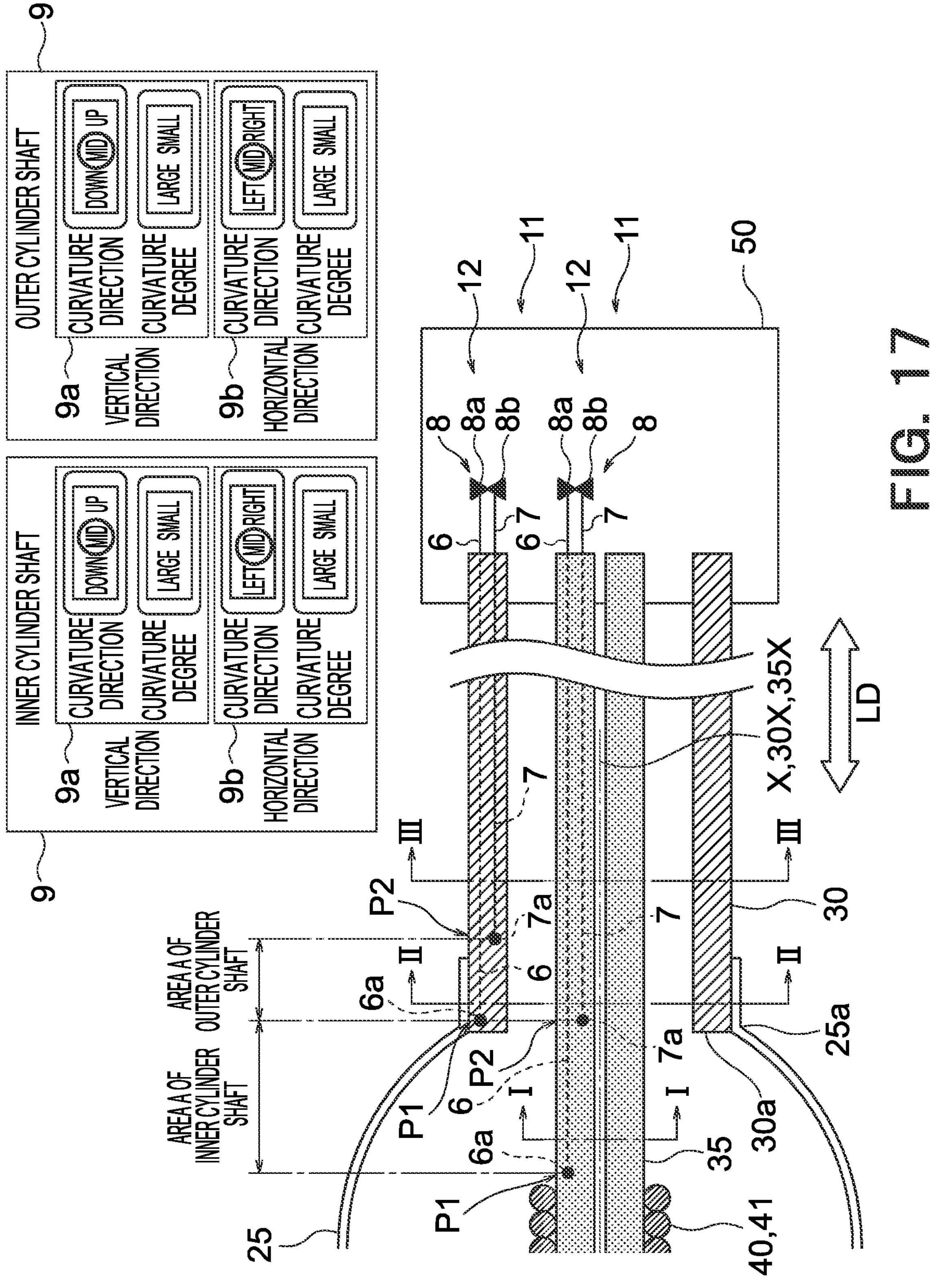
FIG. 17 is a sectional view showing the distal end portion and a proximal end portion of a catheter body of the balloon catheter shown in FIG. 14.
Figure 18A:
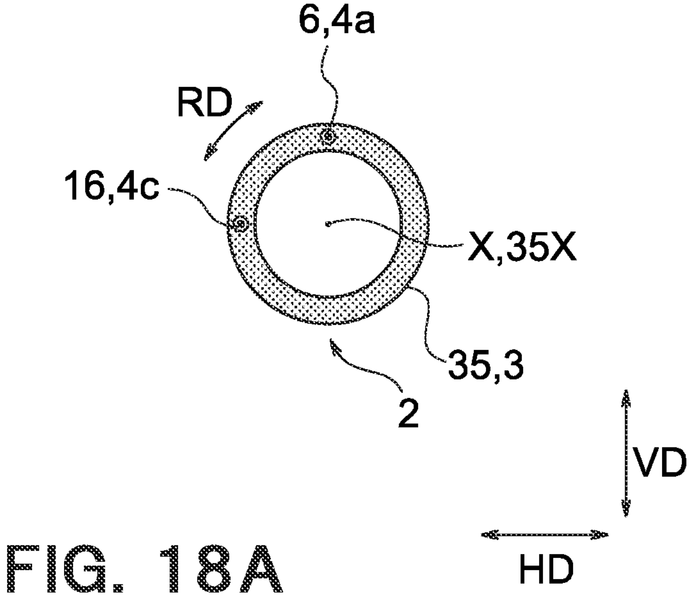
FIG. 18A is a sectional view of the catheter body of FIG. 17 along a I-I line thereof.
Figure 18B:
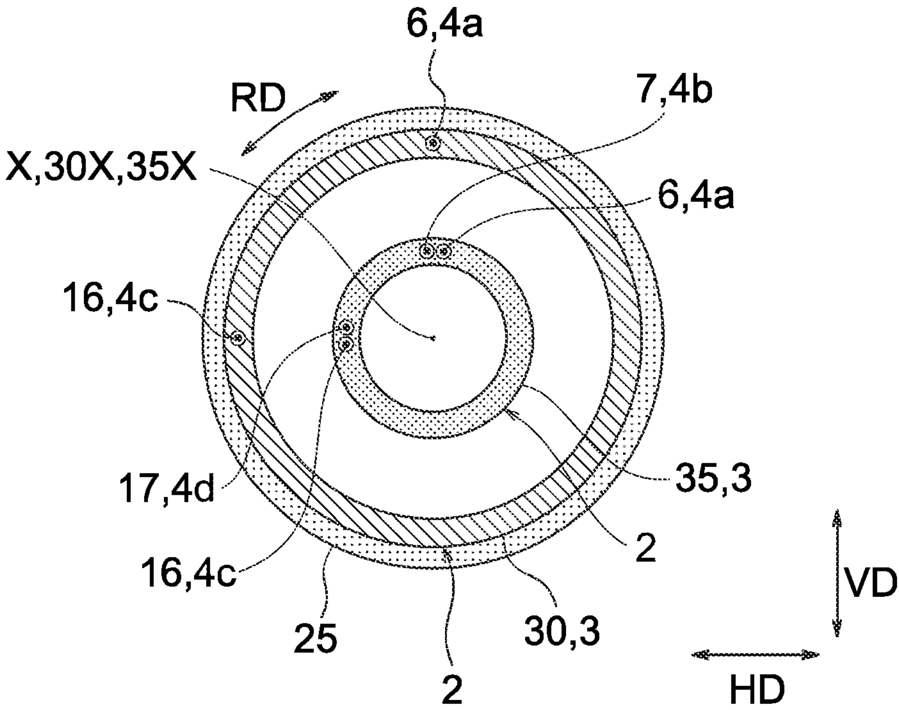
FIG. 18B is a sectional view of the catheter body of FIG. 17 along a II-II line thereof.
Figure 18C:
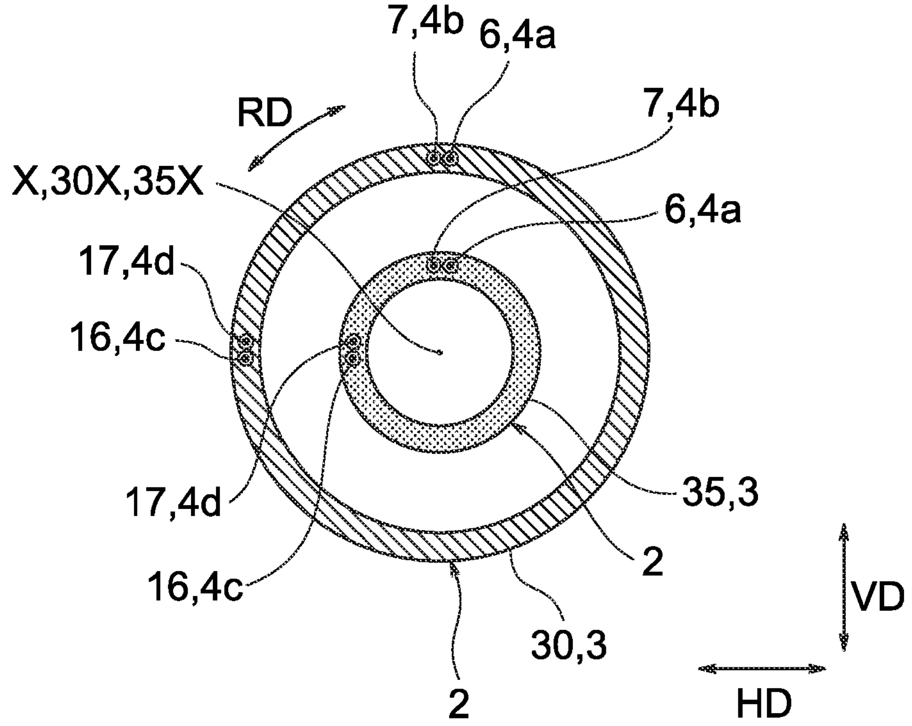
FIG. 18C is a sectional view of the catheter body of FIG. 17 along a line thereof.

In consideration of these issues, as shown in FIGS. 17 to 18C, the balloon catheter 21 in this example includes, as the inner cylinder shaft 35, the base member with the curvature detection function 12 shown in FIGS. 7 to 12. This enables a surgeon to easily detect a curvature state (curvature direction and curvature degree) of the inner cylinder shaft 35 on a constant basis. FIG. 17 shows only the first linear member 6 and the second linear member 7 among the linear members 6, 7, 16, 17. In addition, FIG. 17 omits illustration of lumens 4*a*, 4*b*, 4*c*, 4*d*.

In the illustrated example, the one-side end of the base member 3 of the base member with the curvature detection function 12 is defined as the proximal end of the inner cylinder shaft 35, and the other-side end of the base member 3 is defined as the distal end of the inner cylinder shaft 35. The first fixed position P1 is located at a position overlapping the proximal end 40*b* of the heating member 40, when viewed in a radial direction of a circle centered on the center axis X of the base member 3 (or center axis 35X of the inner cylinder shaft 35). The second fixed position P2 is located at a position overlapping the distal end 35*a* of the outer cylinder shaft 30 with the balloon 25 being inflated, when viewed in a radial direction of a circle centered on the center axis X of the base member 3. Such an inner cylinder shaft 35 makes it possible to detect curvature of the inner cylinder shaft 35 between the heating member 40 and the distal end 30*a* of the outer cylinder shaft 30 on a constant basis, during cautery of a target site with the balloon 25 being inflated. Then, a posture of the distant end of the inner cylinder shaft 35 can be corrected by operating the balloon catheter 21 based on the detected curvature state (curvature direction and curvature degree) of the inner cylinder shaft 35.

In particular, in the illustrated example, the balloon catheter system 20 includes the distance displacement sensors 8, 18 connected to the linear members 6, 7, 16, 17 of the inner cylinder shaft 35, and the display device 9 that receives a signal inputted by the distance displacement sensors 8, 18. Thus, a surgeon can see the displays 9*a*, 9*b* of the display device 9 to find out the curvature state of the inner cylinder shaft 35. FIG. 17 only shows the distance displacement sensor 8 among the distance displacement sensors 8, 18 of the inner cylinder shaft 35. The distance displacement sensors 8, 18 of the inner cylinder shaft 35 are electrically connected to the display device 9 via the connector 56.

Further, in the illustrated example, as shown in FIGS. 17 to 18C, the base member 12 with the curvature detection function 12 shown in FIGS. 7 to 12 is used as the outer cylinder shaft 35. This enables a surgeon to easily find out a curvature state (curvature direction and curvature degree) of the outer cylinder shaft 30 on a constant basis.

In the illustrated example, the one-side end of the base member 3 of the base member with the curvature detection function 12 is defined as the proximal end of the outer cylinder shaft 30, and the other-side end of the base member 3 is defined as the distal end of the outer cylinder shaft 30. The first fixed position P1 of the outer cylinder shaft 30 is located at the distal end of the outer cylinder shaft 30. The second fixed position P2 of the outer cylinder shaft 30 is located on the proximal end side of the distal end 30*a* of the outer cylinder shaft 30. A distance between the first fixed position P1 and the second fixed position P2 in the outer cylinder shaft 30 is, for example, between 1 mm or more and 150 mm or less. Such an outer cylinder shaft 30 makes it possible to detect curvature of the outer cylinder shaft 30 in the vicinity of the distal end 30*a* on a constant basis, to find out, based on the detection, a pressing direction of the balloon 25 against a target site on a constant basis. Thus, a posture of the distant end of the outer cylinder shaft 30 and a pressing direction of the balloon 25 against a target site can be corrected by operating the balloon catheter 21 based on the detection of curvature state (curvature direction and curvature degree) of the outer cylinder shaft 30.

In particular, in the illustrated example, the balloon catheter system 20 includes the distance displacement sensors 8, 18 connected to the linear members 6, 7, 16, 17 of the outer cylinder shaft 30, and the display device 9 that receives a signal inputted by the distance displacement sensors 8, 18. Thus, a surgeon can see the displays 9*a*, 9*b* of the display device 9 to find out the curvature state of the outer cylinder shaft 30. FIG. 17 only shows the distance displacement sensor 8 among the distance displacement sensors 8, 18 of the outer cylinder shaft 30. The distance displacement sensors 8, 18 of the outer cylinder shaft 30 are electrically connected to the display device 9 via the connector 56.

When the base member with the curvature detection function 12 is used as the inner cylinder shaft 35 and/or the outer cylinder shaft 30 of the balloon catheter 21, a diameter of the linear member 6, 7, 16, 17 is preferably between 0.1 mm or more and 0.5 mm or less. Further, in this example, a metal wire made of a corrosion-resistant metal such as SUS 304 or nickel, or a resin monofilament with low-stretch and high strength can be used for the linear member 6, 7, 16, 17.

Next, an example of the use of the balloon catheter system 20 as structured above is described.

First, the inner cylinder shaft 35 is relatively moved with respect to the outer cylinder shaft 30 to the distal side (distant side) in the longitudinal direction LD so that the balloon 25 is stretched as shown in FIG. 16. The outer cylinder shaft 30 and the inner cylinder shaft 35 can be relatively moved by operating the first handle part 51 and the second handle part 52 of the handle 50. Then, the catheter body 22 with the balloon 25 stretched is inserted into the patient's body. When the catheter body 22 is inserted into the patient's body, the balloon 25 is not filled with a liquid.

Next, the distal end of the catheter body 22 is guided close to a target site (affected area), and then the inner cylinder shaft 35 is relatively moved with respect to the outer cylinder shaft 30 to the proximal side (near side) in the longitudinal direction LD so that the balloon 25 is loosened.

Then, the valve 58 is operated to communicate the supply device 74 with the liquid delivery path LP of the catheter body 22. Thereafter, the supply device 74 is operated to let a liquid to flow into the liquid delivery path LP so that the balloon 25 is inflated with the liquid as shown in FIG. 15.

Then, the valve 58 is operated to shut off the supply device 74 from the liquid delivery path LP, and to communicate the agitation device 75 with the liquid delivery path LP. The agitation device 75 is controlled by a control signal from the not-shown agitation-device controller, such that the agitation device 75 repeats supply of a predetermined amount of liquid to the liquid delivery path LP and discharge of a predetermined amount of liquid from the liquid delivery path LP at a regular cycle. This results in repeated ejection of the predetermined amount of liquid from the liquid delivery path LP into the balloon 25 and suction of the predetermined amount of liquid from inside the balloon 25 to the liquid delivery path LP at a regular cycle. Thus, the liquid in the balloon 25 is agitated.

Also, a liquid temperature in the balloon 25 is adjusted by controlling the heating member 40 by the high-frequency current conduction controller 71 of the heating device 70. Specifically, by the heating device 70, a high-frequency voltage is applied between the coil electrode 41 of the heating member 40 and the counter electrode 77 disposed outside the patient's body. As a result, a high-frequency current flows between the coil electrode 41 and the counter electrode 77.

The liquid in the balloon 25 is agitated while being heated as described above. Then, the balloon containing the heated liquid is pressed against the target site to ablate the target site.

During the ablation, the catheter body 22 is operated to correct a pressing direction of the balloon 25 against the target site, observing a curvature state close to the distal end 30*a* of the outer cylinder shaft 30, which is displayed on the displays 9*a*, 9*b* of the display device 9. In addition, observing a curvature state of the inner cylinder shaft 30 between the coil electrode 41 and the distal end 30*a* of the outer cylinder shaft 30 displayed on the displays 9*a*, 9*b* of the display device 9, the catheter body 22 is operated to adjust a direction along which the coil electrode 41 and the distal end 30*a* of the outer cylinder shaft 30 are aligned so that the direction of the alignment matches a direction along which the center axis 30X of the outer cylinder shaft 30 in the distal end 30*a* of the outer cylinder shaft 30 extends.

The use of such a balloon catheter 21 allows a surgeon to easily press the balloon 25 against a target site in a proper direction. In addition, it is easy to correct a posture of the distant end of the inner cylinder shaft 35 to effectively agitate a liquid in the balloon 25. Thus, it is easy to adjust a surface temperature of the balloon, which is one of the most important factors in the ablation therapy, to an ideal temperature. This can significantly improve the ablation therapy effect.

Upon completion of the ablation to the target site, energy supply to the heating member 40 is stopped. In addition, the valve 58 is operated so that the supply device 74 is communicated with the liquid delivery path LP of the catheter body 22 through the handle 50, and that the agitation device 75 is shut off from the liquid delivery path LP. Then, the liquid is discharged by the supply device 74 from the liquid delivery path LP to deflate the balloon 25. Then, the second handle part 25 is operated to stretch the deflated balloon 25 as shown in FIG. 16. After that, the catheter body 22 with the balloon 25 stretched is pulled out from the patient's body. In this manner, the procedure using the balloon catheter system 20 is completed.

The base member with the curvature detection function 2, 12, 102, the curvature detection system 1, 11, 101, and the balloon catheter system 20 to which the curvature detection system 1, 11, 101 is applied have been described above, with reference to FIGS. 1 to 18C, 19 and 20. However, the base member with the curvature detection function 2, 12, 102, the curvature detection system 1, 11, 101, and the balloon catheter system 20 are not limited to the structures described above. The base member with the curvature detection function 2, 12, 102, the curvature detection system 1, 11, 101, and the balloon catheter system 20 shown in FIGS. 1 to 18C can be variously changed in structure.

For example, in the examples shown in FIGS. 1 to 18C, the first linear member 6 and the second linear member 7 are disposed in the separate lumens 4*a*, 4*b*, but they may be disposed in the same lumen. The first linear member 6 and the second linear member 7 may not be disposed in the lumens 4*a*, 4*b*, but may be disposed on a surface of the base member 3. In addition, in the examples shown in FIGS. 7 to 12 and 14 to 18C, the third linear member 16 and the fourth linear member 17 are disposed in the separate lumens 4*c*, 4*d*, but they may be disposed in the same lumen. The third linear member 16 and the fourth linear member 17 may not be disposed in the lumens 4*c*, 4*d*, but may be disposed on the surface of the base member 3. In the example shown in FIG. 13, the fifth linear member 108 is disposed in the lumen 4*e* separated from the lumens 4*a*, 4*b* of the first linear member 6 and the second linear member 7, but the linear members 6, 7, 108 may be disposed in the same lumen. The linear members 6, 7, 108 may not be disposed in the lumens 4*a*, 4*b*, 4*e*, but may be disposed on the surface of the base member 3.

In the examples shown in FIGS. 7 to 12 and 14 to 18C, the display device 9 displays the curvature direction of the base member 3 as two pieces of information, i.e., the vertical direction and the horizontal direction, but this disclosure is not limited thereto. The display device 9 may computes a signal inputted by the distance displacement sensor 8 and a signal inputted by the second distance displacement sensor 18, and may display one curvature direction in which the curvature direction of the base member in the vertical direction and the curvature direction thereof in the horizontal direction are combined in one. This allows a surgeon to more easily understand the curvature direction of the base member 3.

In the examples shown in FIGS. 1 to 18C, the display device 9 displays the curvature direction and the curvature degree of the base member 3 by characters, but this disclosure is not limited thereto. The display device 9 may show the curvature direction by an image, a chart, a vector or the like. In particular, when the curvature direction of the base member 3 is shown as one curvature direction in which the curvature direction of the base member in the vertical direction and the curvature direction thereof in the horizontal direction are combined, the display device 9 preferably displays the curvature direction by an image, a chart, a vector or the like.

In the examples shown in FIGS. 1 to 18C, change in a relative position between the second ends 6*b*, 7*b*; 16*b*, 17*b*; 6*b*, 7*b*, 108*b* is detected by the distance displacement sensor 8, 18, but this disclosure is not limited thereto. For example, change in a relative position between the second ends 6*b*, 7*b*; 16*b*, 17*b*; 6*b*, 7*b*, 108*b* may be detected by a pressure sensor. In this example, change in a relative position between the second ends 6*b*, 7*b*; 16*b*, 17*b*; 6*b*, 7*b*, 108*b* may be detected by detecting a difference between tensile forces or pressing forces applied by the linear members 6, 7; 16, 17; 6, 7, 108. A proximity sensor or the like may be employed as a sensor that detects change in a relative position between the second ends 6*b*, 7*b*; 16*b*, 17*b*; 6*b*, 7*b*, 108*b*.

A change in a relative position between the second ends 6*b*, 7*b*; 16*b*, 17*b* may be detected by markers provided on the surfaces of the linear member 6, 16 and the linear member 7, 17, i.e., by observing change in a relative position between the marker provided on the linear member 6, 16 and the marker provided on the linear member 7, 17. One marker may be a distance measuring scale capable of measuring a relative movement distance of the other marker. These markers may be provided on other members fixed to the linear member 6, 16 and the linear member 7, 17. A change in a relative position between the second ends 17*b*, 108*b* may also be detected by markers.

Further, the curvature detection system 1, 11, 101 may comprise an alarm which issues a warning that curvature has occurred.

Application of the aforementioned curvature detection system 1, 11, 101 and the base member with the curvature detection function 2, 12, 102 is not limited to a balloon catheter. The base member with the curvature detection function 2, 12, 102 may be applied to a catheter of another type or another medical device such as a medical endoscope. Further, the base member with the curvature detection function 2, 12, 102 may be applied to a device other than a medical device such as an industrial endoscope.

In the aforementioned first to third examples, the base member with the curvature detection function 2, 12, 102 comprises the base member 3 having the longitudinal direction LD, the first linear member 6 extending along the longitudinal direction LD, and the second linear member 7 extending along the longitudinal direction LD. The first linear member 6 is fixed to the base member 3 at the first fixed position P1, and is relatively movable with respect to the base member 3 in the longitudinal direction LD, on the one side of the first fixed position P1 in the longitudinal direction LD. The second linear member 7 is fixed to the base member 3 at the second fixed position P2 apart from the first fixed position P1 in the longitudinal direction LD, and is relatively movable with respect to the base member 3 in the longitudinal direction LD, on the one side of the second fixed poison P2 in the longitudinal direction LD. The base member with the curvature detection function 2, 12, 102 is capable of detecting curvature of the base member 3 between the first fixed position P1 and the second fixed position P2 based on change in a relative position between the first linear member 6 and the second linear member 7.

In the first to third examples, the first linear member 6 and the second linear member 7 are disposed in one or more lumens 4*a*, 4*b* provided in the base member 3. This can reduce the risk of damaging the linear members 6, 7 and preventing the base member with the curvature detection function 2, 12, 102 from detecting curvature of the base member 3.

In the first to third examples, the first linear member 6 and the second linear member 7 are disposed in the separate lumens 4*a*, 4*b*. This can reduce the risk of causing the linear members 6, 7 to be entangled and preventing the base member with the curvature detection function 2, 12, 102 from detecting curvature of the base member 3.

In the first to third examples, the base member 3 is a cylindrical member having the wall 4 delimiting the hollow. Such a shape of the base member 3 allows the base member with the curvature detection function 2 to be applied to a catheter, an endoscope, and so on.

In the first to third examples, the lumens 4*a*, 4*b* are formed in the wall 4. This can minimize increase in size of the base member 3 due to the formation of the lumens 4*a*, 4*b*.

In the modification example, markers indicating a relative position between the first linear member 6 and the second linear member 7 are provided on the first linear member 6 and the second linear member 7. This allows curvature of the base member 3 to be easily detected.

In the second example, the base member with the curvature detection function 12 comprises the third linear member 16 and the fourth linear member 17 which extend along the longitudinal direction LD at a position apart from a position of the first linear member 6 and the second linear member 7 in the circumferential direction RD of the wall 4. The third linear member 16 is fixed to the base member 3 at the first fixed position P1, and is relatively movable with respect to the base member 3 in the longitudinal direction LD, on the one side of the first fixed position P1 in the longitudinal direction LD. The fourth member 17 is fixed to the base member 3 at the second fixed position P2, and is relatively movable with respect to the base member 3 in the longitudinal direction LD, on the one side of the second fixed poison P2 in the longitudinal direction. The base member with the curvature detection function 12 is capable of detecting curvature of the base member 3 between the first fixed position P1 and the second fixed position P2 based on change in a relative position between the third linear member 16 and the fourth linear member 17. In particular, the base member with the curvature detection function 12 is also capable of detecting curvature whose direction is different from that of the curvature detected based on change in a relative position between the first linear member 6 and the second linear member 7.

Specifically, in the second example, the third linear member 16 and the fourth linear member 18 are disposed in other one or more lumens 4*c*, 4*d* which are separated from the one or more lumens 4*a*, 4*b* for the first linear member 6 and the second linear member 7. The other one or more lumens 4*c*, 4*d* are provided at a position apart from the position of the one or more lumens 4*a*, 4*b* in the circumferential direction RD of the wall 4. This can reduce the risk of causing the linear members 6, 7 and the linear members 16, 17 to be entangled and preventing the base member with the curvature detection function 12 from detecting curvature in the aforementioned two directions. In addition, since the linear members 16, 17 are disposed in the one or more lumens 4*c*, 4*d*, the risk of damaging the linear members 16, 17, and preventing the base member with the curvature detection function 12 from detecting curvature of the base member 3, can be reduced.

In the modification example, markers indicating a relative position between the third linear member 16 and the fourth linear member 17 are provided on the third linear member 16 and the fourth linear member 17. This allows curvature of the base member 3 to be easily detected.

In the first to third examples, the curvature detection system 1, 11, 101 comprises the aforementioned base member with the curvature detection function 2, 12, 102, and the sensor 8 configured to detect change in a relative position between the first linear member 6 and the second linear member 7. Such a curvature detection system 1 can easily detect curvature of the base member 3.

In the second example, the curvature detection system 11 comprises the aforementioned base member with the curvature detection function 12, the sensor 8 configured to detect change in a relative position between the first linear member 6 and the second linear member 7, and the second sensor 18 configured to detect change in a relative position between the third linear member 16 and the fourth linear member 17. Such a curvature detection system 1 can easily detect curvature of the base member in two directions different from each other.

In the modification example, the device comprises the aforementioned base member with the curvature detection function 2, 12, 102. Such a device can detect curvature of the base member 3 in a location difficult to see, which improves operability of the device.

In the aforementioned application example, the balloon catheter 21 comprises the balloon 25, the catheter body 22, and the heating member 40. The catheter body 22 has the outer cylinder shaft 30 connected to the proximal end 25*b* of the balloon 25, and the inner cylinder shaft 35 extending into the balloon 25 to be connected to the distal end 25*a* of the balloon 25. The inner cylinder shaft 35 extends inside the outer cylinder shaft 30. The gap between the inner cylinder shaft 35 and the outer cylinder shaft 30 serves as the liquid delivery path LP in communication with the inside space of the balloon 25. The heating member 40, which is for heating a liquid in the balloon 25, is disposed on the outer circumferential surface of the inner cylinder shaft 35 in the balloon 25. The inner cylinder shaft 35 is the aforementioned base member with the curvature detection function 2, 12, 102. Such a balloon catheter 21 makes it possible to detect curvature of the inner cylinder shaft 35 disposed in a human body, which improves operability of the balloon catheter 21.

My concepts can be used in a variety of devices. For example, my base members can be used in a catheter such as a balloon catheter for treating arrhythmias such as atrial fibrillation, endometriosis, cancer and the like, a medical device such as a medical endoscope, and an industrial device such as an industrial endoscope.

The invention claimed is:

1. A curvature detection system comprising:

a base member having a longitudinal direction, wherein the base member is a cylindrical member having a wall delimiting a hollow;

a first linear member extending in the longitudinal direction, wherein the first linear member is fixed to the base member at a first fixed position, and is relatively movable with respect to the base member in the longitudinal direction, on one side of the first fixed position in the longitudinal direction;

a second linear member extending in the longitudinal direction, wherein the second linear member is fixed to the base member at a second fixed position different from the first fixed position, and is relatively movable with respect to the base member in the longitudinal direction, on the one side of the second fixed position in the longitudinal direction;

a distance displacement sensor, wherein the sensor is configured to detect change in a relative position between the first linear member and the second linear member, thereby detecting curvature of the base member between the first fixed position and the second fixed position based on change in the relative position between the first linear member and the second linear member;

a third linear member; and a fourth linear member, wherein the third and fourth linear members extend along the longitudinal direction at a position different from a position of the first linear member and the second linear member in a circumferential direction of the wall, the third linear member is fixed to the base member at the first fixed position, and is relatively movable with respect to the base member in the longitudinal direction, on the one side of the first fixed position in the longitudinal direction, the fourth linear member is fixed to the base member at the second fixed position, and is relatively movable with respect to the base member in the longitudinal direction, on the one side of the second fixed position in the longitudinal direction, the system is capable of detecting curvature of the base member between the first fixed position and the second fixed position based on change in a relative position between the third linear member and the fourth linear member, the first linear member and the second linear member are disposed in one or more lumens provided in the base member, and the third linear member and the fourth linear member are disposed in other one or more lumens provided at a position different from a position of the one or more lumens for the first linear member and the second linear member in the circumferential direction of the wall.

2. The curvature detection system according to claim 1, wherein the first linear member and the second linear member are disposed in one or more lumens provided in the base member.

3. The curvature detection system according to claim 2, wherein the first linear member and the second linear member are disposed in separate lumens.

4. The curvature detection system according to claim 1, wherein the first linear member and the second linear member are disposed in one or more lumens provided in the base member, and the one or more lumens are formed in the wall.

5. The curvature detection system according to claim 1, wherein markers indicating a relative position between the first linear member and the second linear member are provided on the first linear member and the second linear member.

6. The curvature detection system according to claim 1, wherein markers indicating a relative position between the third linear member and the fourth linear member are provided on the third linear member and the fourth linear member.

7. The curvature detection system according to claim 1, comprising:

a second sensor configured to detect change in a relative position between the third linear member and the fourth linear member.

8. A balloon catheter system comprising:

a balloon;

a base member having a longitudinal direction, wherein the base member is a cylindrical member having a wall delimiting a hollow;

a catheter shaft having an outer cylinder shaft connected to a proximal end of the balloon, an inner cylinder shaft having a longitudinal direction and extending into the balloon to be connected to a distal end of the balloon, a first linear member extending in the longitudinal direction, and a second linear member extending in the longitudinal direction, wherein the inner cylinder shaft extends inside the outer cylinder shaft, a gap between the inner cylinder shaft and the outer cylinder shaft serves as a liquid delivery path in communication with an inside space of the balloon, the first linear member is fixed to the base member at a first fixed position and is relatively movable with respect to the base member in the longitudinal direction, on one side of the first fixed position in the longitudinal direction, and the second linear member is fixed to the base member at a second fixed position different from the first fixed position and is relatively movable with respect to the base member in the longitudinal direction, on the one side of the second fixed position in the longitudinal direction;

a heating member that heats a liquid in the balloon, the heating member being disposed on an outer circumferential surface of the inner cylinder shaft in the balloon; and a distance displacement sensor, wherein the sensor is configured to detect change in a relative position between the first linear member and the second linear member, thereby detecting curvature of the base member between the first fixed position and the second fixed position based on change in the relative position between the first linear member and the second linear member.

9. A curvature detection system, comprising:

a base member having a longitudinal direction;

a first linear member extending in the longitudinal direction, wherein the first linear member is fixed to the base member at a first fixed position, and is relatively movable with respect to the base member in the longitudinal direction, on one side of the first fixed position in the longitudinal direction;

a second linear member extending in the longitudinal direction, wherein the second linear member is fixed to the base member at a second fixed position different from the first fixed position, and is relatively movable with respect to the base member in the longitudinal direction, on the one side of the second fixed position in the longitudinal direction; and a distance displacement sensor, wherein the sensor is configured to detect change in a relative position between the first linear member and the second linear member, thereby detecting curvature of the base member between the first fixed position and the second fixed position based on change in the relative position between the first linear member and the second linear member, and comprises a first sensor at a second, unfixed, end of the first linear member and a second sensor at a second, unfixed end, of the second linear member.

* * * * *